(12) United States Patent
Querellou et al.

(10) Patent No.: US 6,673,585 B1
(45) Date of Patent: Jan. 6, 2004

(54) HEAT-STABLE DNA POLYMERASE OF ARCHAEOBACTERIA OF GENUS PYROCOCCUS SP.

(75) Inventors: Joel Querellou, Brest (FR); Marie Anne Cambon, Plouzane (FR)

(73) Assignee: Appligene-Oncor S.A., Illkirch (FR)

( * ) Notice: Subject to any disclaimer, the term of this patent is extended or adjusted under 35 U.S.C. 154(b) by 0 days.

(21) Appl. No.: 09/214,916

(22) PCT Filed: Jul. 10, 1997

(86) PCT No.: PCT/FR97/01259

§ 371 (c)(1),
(2), (4) Date: Sep. 7, 1999

(87) PCT Pub. No.: WO98/01567

PCT Pub. Date: Jan. 15, 1998

(30) Foreign Application Priority Data

Jul. 10, 1996 (FR) .............................. 96 08631

(51) Int. Cl.$^7$ .............................. C12N 9/12; C07H 21/04
(52) U.S. Cl. ...................... 435/194; 435/183; 530/350; 530/358; 536/23.1; 536/23.2; 536/23.7
(58) Field of Search .................... 435/194, 183; 530/350, 358; 536/23.1, 23.2, 23.7

(56) References Cited

FOREIGN PATENT DOCUMENTS

| EP | 0547359 | 6/1993 |
|---|---|---|
| EP | 0547920 | 6/1993 |
| EP | 0624641 | 11/1994 |
| EP | 0701000 | 3/1996 |
| EP | 0745675 | 12/1996 |
| WO | 9209689 | 6/1992 |
| WO | WO 92/09689 | * 6/1992 |

OTHER PUBLICATIONS

M. Cambon et al., "Cloning, sequencing and expression of DNA dependent DNA polymerase from hyperthermophilic archaeon *Pyrococcus abyssi*", *EMBL Sequence Data Base*, Sep. 14, 1995, Heidelberg, Brd. XP002055719, Accession No. Z54174.

G. Erauso et al, "Sequence of plasmid pGT5 from the archeon *Pyrococcus abyssi*: Evidence for rolling–circle replication in a hyperthermophile," *J. Bacteriol*:718(11): 3232–3237 (Jun. 11, 1996).

V. T. Marteinsson et al., "Phenotypic characterization, DNA similarities, and protein profiles of twenty sulfur–metabolizing hyperthermophilic anaerobic archaea isolated from hydrothermal vents in the southwestern pacific ocean," *International Journal of Systemic Bacteriology*:45(4): 623–632 (Oct., 1995) XP000645354.

C. Purcarea et al., "The catalytic and regulatory properties of asparatate transcarbasmylase from *Pyrococuus abyassi*, a new deep–sea hyperthermophilic archaeobacterium," *Microbiology*:140(8):1967–1975 (1994) XP000645351.

G. Erauso, et al., "*Pyrococcus abyssi sp.* nov., a hyperthermophilic archaeon isolated from a deep–sea hydrothermal vent," *Archives of Microbiology*, 160 (5):338–349 (1993) XP000645347.

M. Cambon et al., "Molecular cloning and sequencing of DNA dependent DNA polymerase from a new hyperthermophilic isolate *Pyrococcus sp.* strain GE23", *EMBL Sequence Database*, Aug. 17, 1996, Heidelberg, Frg., XP002055720 Accession No. Z54173.

* cited by examiner

*Primary Examiner*—Richard Hutson
(74) *Attorney, Agent, or Firm*—Hoffmann & Baron, LLP; Irving N. Feit

(57) ABSTRACT

A purified thermostable DNA polymerase of archaeobacteria of the genus Pyrococcus sp. having a molecular weight of around 89,000–90,000 daltons is disclosed.

4 Claims, 17 Drawing Sheets

SEQUENCE LISTING

<160> NUMBER OF SEQ ID NOS: 10

<210> SEQ ID NO 1
<211> LENGTH: 4446
<212> TYPE: DNA
<213> ORGANISM: archaeoboacteria pyroccocus
<220> FEATURE:
<221> NAME/KEY: CDS
<222> LOCATION: (1547)..(3862)
<221> NAME/KEY: stop codon
<222> LOCATION: (3860)..(3862)

<400> SEQUENCE: 1

| | | | | | |
|---|---|---|---|---|---|
| cgaagatgag | agatttggtg | gaatgccgac | ttacgggcaa | gaaatttgag | agagataaaa | 60 |
| tcaacgttaa | gatagcggtg | gcctattctg | gaggaagcga | tagctcagcc | acagtaaaga | 120 |
| tactgagatg | ggctggcttt | gatgtggtcc | caataacggc | gaggcttccc | cacataagca | 180 |
| aagaggagtt | acgggaagaa | actctattcg | tggaagttcc | tgggtacctt | gaggagatgg | 240 |
| agaggttaat | agaaaagagg | gccccctatct | gtggaaggtg | ccactctatg | gttatgagag | 300 |
| ctgttgcgag | aaaaggttag | ggagcttaaa | ataagaatac | tcgctactgg | agacatgctc | 360 |
| agcataggaa | gcgggtcaat | ctacgagaaa | gaaaatcttg | tgattttgaa | cttaccagct | 420 |
| ttcctatcac | taaacaaggt | tgaccttctg | agcatactag | gctgggagga | ttatgagttt | 480 |
| aagtatggat | gcccccttttg | gagggaggcc | gtgaaaaggg | ctccaataat | gaagaggttt | 540 |
| gcaatccaga | gggttctgag | ggaattgagg | gcaggggcaa | taaacgagaa | tattgctaag | 600 |
| aaacttattt | ttgatatatt | aagggcctaa | acgaacctcg | ccggtctgag | ggttttcact | 660 |
| ttaatttcct | tgtctatcgt | aaccctgaac | ccttccttgg | ccacataggt | tttcacgccg | 720 |
| gtaacgtttt | ggatatactg | ggcctcctta | tagggaccag | cgaagtgcat | cttcatgccg | 780 |
| agatgcgtca | tcacgagaac | ttcaggcctt | tgcttcattg | cctttagcat | gtaaactatg | 840 |
| tcgtcggttg | ataagtggta | gggaatcttc | atgtccctgg | gcctcgttac | tgaggctatc | 900 |
| aaaactctcg | acccatcatg | ccagcttacc | agctctggaa | aatactcagt | atccgctatg | 960 |
| tacgagatat | ccccaaggct | ggtttttaat | ctaaagccta | tcgttgttga | gtcgctgtgc | 1020 |
| tgggatggag | ttattatcat | ctcctcattt | cctaacctaa | acctgtcccc | aggattgggg | 1080 |
| gcatggactt | cctctaatgc | ctccaagtgg | tacttgctca | gggctggggt | atgatcctcg | 1140 |
| cccccataaa | acacgcttct | agaacctatt | agggttcccc | tcttcttagt | aacaccgtat | 1200 |
| gtcattccca | caacgaacac | ctcggcggcg | gtggagtgat | cggtgtgtct | atgcgaaatg | 1260 |
| aagagaacat | ctatcttcct | ggggtctaac | ttgtatctaa | tcatcctaac | tagcgctcca | 1320 |
| ggcccaggat | ccacaaagat | attttttgctt | gccttgatga | agaatccccc | tgtggatctt | 1380 |
| acttgagtta | tcgtcacgaa | cctgccccca | ccggcaccca | agaacgtaat | ctctatcatt | 1440 |
| tttagtcccg | aaattaaagt | gcgaggctta | tgcttttaag | gatgtatggc | gaaaggtgaa | 1500 |
| gtttattaga | agttagaatc | taaagatttc | agattgggtg | ggggta atg ata atc | | 1555 |
| | | | | Met Ile Ile | |
| | | | | 1 | |

| gat | gct | gat | tac | ata | acg | gaa | gat | ggc | aag | ccg | ata | ata | aga | ata | ttc | 1603 |
|---|---|---|---|---|---|---|---|---|---|---|---|---|---|---|---|---|
| Asp | Ala | Asp | Tyr | Ile | Thr | Glu | Asp | Gly | Lys | Pro | Ile | Ile | Arg | Ile | Phe | |
| | 5 | | | | 10 | | | | | 15 | | | | | | |

| aaa | aag | gaa | aag | gga | gag | ttt | aag | gta | gaa | tac | gat | agg | acg | ttt | aga | 1651 |
|---|---|---|---|---|---|---|---|---|---|---|---|---|---|---|---|---|
| Lys | Lys | Glu | Lys | Gly | Glu | Phe | Lys | Val | Glu | Tyr | Asp | Arg | Thr | Phe | Arg | |
| 20 | | | | 25 | | | | | 30 | | | | | 35 | | |

-continued

| | |
|---|---|
| ccc tac att tac gct ctt tta aag gat gat tcg gcc ata gat gag gtt<br>Pro Tyr Ile Tyr Ala Leu Leu Lys Asp Asp Ser Ala Ile Asp Glu Val<br>40          45              50 | 1699 |
| aag aag ata acc gcc gag agg cac gga aag ata gtc agg ata acc gaa<br>Lys Lys Ile Thr Ala Glu Arg His Gly Lys Ile Val Arg Ile Thr Glu<br>    55              60              65 | 1747 |
| gtt gag aaa gtc cag aag aaa ttc cta gga agg cca ata gaa gtc tgg<br>Val Glu Lys Val Gln Lys Lys Phe Leu Gly Arg Pro Ile Glu Val Trp<br>        70              75              80 | 1795 |
| aag ctg tac ctt gag cat cca caa gac gtt cca gct atc aga gag aag<br>Lys Leu Tyr Leu Glu His Pro Gln Asp Val Pro Ala Ile Arg Glu Lys<br>            85              90              95 | 1843 |
| ata agg gaa cat cca gct gta gtt gat ata ttc gaa tac gac ata ccc<br>Ile Arg Glu His Pro Ala Val Val Asp Ile Phe Glu Tyr Asp Ile Pro<br>100             105             110             115 | 1891 |
| ttt gcg aaa cgc tac cta ata gat aag gga ttg act cca atg gag ggg<br>Phe Ala Lys Arg Tyr Leu Ile Asp Lys Gly Leu Thr Pro Met Glu Gly<br>        120             125             130 | 1939 |
| aac gag gag cta acg ttt cta gca gtt gac ata gaa aca ttg tac cat<br>Asn Glu Glu Leu Thr Phe Leu Ala Val Asp Ile Glu Thr Leu Tyr His<br>            135             140             145 | 1987 |
| gaa gga gag gag ttc ggg aaa ggc cct ata atc atg atc agc tac gcc<br>Glu Gly Glu Glu Phe Gly Lys Gly Pro Ile Ile Met Ile Ser Tyr Ala<br>150             155             160 | 2035 |
| gac gag gaa ggg gcc aag gtg ata act tgg aag agc ata gac tta cct<br>Asp Glu Glu Gly Ala Lys Val Ile Thr Trp Lys Ser Ile Asp Leu Pro<br>        165             170             175 | 2083 |
| tac gtt gaa gtg gtt tca agc gag agg gag atg ata aag agg ctc gtg<br>Tyr Val Glu Val Val Ser Ser Glu Arg Glu Met Ile Lys Arg Leu Val<br>180             185             190             195 | 2131 |
| aag gta att aga gag aag gat ccc gac gtg ata ata acg tac aat ggt<br>Lys Val Ile Arg Glu Lys Asp Pro Asp Val Ile Ile Thr Tyr Asn Gly<br>            200             205             210 | 2179 |
| gat aat ttc gac ttt ccg tac ctc tta aag agg gct gaa aag ctc gga<br>Asp Asn Phe Asp Phe Pro Tyr Leu Leu Lys Arg Ala Glu Lys Leu Gly<br>        215             220             225 | 2227 |
| ata aag ctc ccc ctt gga agg gac aat agc gag ccg aag atg cag agg<br>Ile Lys Leu Pro Leu Gly Arg Asp Asn Ser Glu Pro Lys Met Gln Arg<br>230             235             240 | 2275 |
| atg ggg gat tca tta gct gta gag ata aag ggc aga ata cac ttc gat<br>Met Gly Asp Ser Leu Ala Val Glu Ile Lys Gly Arg Ile His Phe Asp<br>    245             250             255 | 2323 |
| tta ttc ccc gtc ata aga aga acg atc aac ctt cca aca tac acc ctc<br>Leu Phe Pro Val Ile Arg Arg Thr Ile Asn Leu Pro Thr Tyr Thr Leu<br>260             265             270             275 | 2371 |
| gaa gcg gtt tat gag gct ata ttt gga aag tct aag gag aaa gtc tat<br>Glu Ala Val Tyr Glu Ala Ile Phe Gly Lys Ser Lys Glu Lys Val Tyr<br>            280             285             290 | 2419 |
| gcc cat gag ata gct gag gcc tgg gaa acc ggg aaa ggg cta gag agg<br>Ala His Glu Ile Ala Glu Ala Trp Glu Thr Gly Lys Gly Leu Glu Arg<br>        295             300             305 | 2467 |
| gta gct aag tat tca atg gaa gat gcg aag gta acc ttt gag ctc gga<br>Val Ala Lys Tyr Ser Met Glu Asp Ala Lys Val Thr Phe Glu Leu Gly<br>310             315             320 | 2515 |
| aag gag ttc ttc cca atg gaa gcc cag cta gct agg ctc gtt ggc cag<br>Lys Glu Phe Phe Pro Met Glu Ala Gln Leu Ala Arg Leu Val Gly Gln<br>    325             330             335 | 2563 |
| cca gtt tgg gac gtt tca agg tcg agc acc gga aac ctc gtt gag tgg<br>Pro Val Trp Asp Val Ser Arg Ser Ser Thr Gly Asn Leu Val Glu Trp<br>340             345             350             355 | 2611 |

-continued

| | |
|---|---|
| ttt ctc ctt agg aag gcc tac gag aga aat gag ctc gcg ccc aat aaa<br>Phe Leu Leu Arg Lys Ala Tyr Glu Arg Asn Glu Leu Ala Pro Asn Lys<br>                        360                          365                370 | 2659 |
| ccg gac gag agg gaa tac gag aga agg cta aga gag agc tat gaa ggg<br>Pro Asp Glu Arg Glu Tyr Glu Arg Arg Leu Arg Glu Ser Tyr Glu Gly<br>                 375                         380                      385 | 2707 |
| ggt tac gtt aag gag cca gag aag gga ttg tgg gaa ggg ata gtc agc<br>Gly Tyr Val Lys Glu Pro Glu Lys Gly Leu Trp Glu Gly Ile Val Ser<br>         390                          395                      400 | 2755 |
| tta gac ttt agg tcc cta tat ccg tct ata att ata act cac aac gtc<br>Leu Asp Phe Arg Ser Leu Tyr Pro Ser Ile Ile Ile Thr His Asn Val<br>405                          410                      415 | 2803 |
| tca cca gac act ttg aat aga gaa aat tgc aag gaa tac gac gtt gcc<br>Ser Pro Asp Thr Leu Asn Arg Glu Asn Cys Lys Glu Tyr Asp Val Ala<br>420                          425                      430                      435 | 2851 |
| ccc caa gtg ggg cac aga ttc tgc aag gat ttc cca gga ttc ata cca<br>Pro Gln Val Gly His Arg Phe Cys Lys Asp Phe Pro Gly Phe Ile Pro<br>                 440                         445                      450 | 2899 |
| agc tta ctg ggt aac tta ctg gag gag aga caa aag ata aaa aag aga<br>Ser Leu Leu Gly Asn Leu Leu Glu Glu Arg Gln Lys Ile Lys Lys Arg<br>         455                          460                      465 | 2947 |
| atg aaa gaa agt aaa gat ccc gtc gag aag aaa ctc ctt gat tac aga<br>Met Lys Glu Ser Lys Asp Pro Val Glu Lys Lys Leu Leu Asp Tyr Arg<br>                 470                         475                      480 | 2995 |
| cag aga gct ata aaa ata ctt gca aac agc tat tat ggc tat tat gga<br>Gln Arg Ala Ile Lys Ile Leu Ala Asn Ser Tyr Tyr Gly Tyr Tyr Gly<br>         485                          490                      495 | 3043 |
| tat gca aag gcc aga tgg tac tgt aag gag tgt gca gag agc gta act<br>Tyr Ala Lys Ala Arg Trp Tyr Cys Lys Glu Cys Ala Glu Ser Val Thr<br>500                          505                      510                      515 | 3091 |
| gca tgg ggg agg caa tac ata gat cta gtt aga aga gag ctt gaa agc<br>Ala Trp Gly Arg Gln Tyr Ile Asp Leu Val Arg Arg Glu Leu Glu Ser<br>                 520                         525                      530 | 3139 |
| agc gga ttc aag gtt ctg tac ata gac act gat ggc ctc tac gcg acc<br>Ser Gly Phe Lys Val Leu Tyr Ile Asp Thr Asp Gly Leu Tyr Ala Thr<br>         535                          540                      545 | 3187 |
| att cct ggg gcc aag cca aat gag ata aaa gaa aag gcc ctt aag ttc<br>Ile Pro Gly Ala Lys Pro Asn Glu Ile Lys Glu Lys Ala Leu Lys Phe<br>                 550                         555                      560 | 3235 |
| gtc gag tac ata aac tcc aag tta cct ggg ctt ctt gaa ttg gaa tac<br>Val Glu Tyr Ile Asn Ser Lys Leu Pro Gly Leu Leu Glu Leu Glu Tyr<br>565                          570                      575 | 3283 |
| gaa ggt ttc tac gcg aga ggg ttc ttc gtg acg aag aaa aag tac gca<br>Glu Gly Phe Tyr Ala Arg Gly Phe Phe Val Thr Lys Lys Lys Tyr Ala<br>580                          585                      590                      595 | 3331 |
| cta atc gac gag gaa gga aag ata gtt acg agg ggg ctc gaa ata gta<br>Leu Ile Asp Glu Glu Gly Lys Ile Val Thr Arg Gly Leu Glu Ile Val<br>                 600                         605                      610 | 3379 |
| agg aga gat tgg agt gaa ata gca aag gag acc caa gct aag gtt ctc<br>Arg Arg Asp Trp Ser Glu Ile Ala Lys Glu Thr Gln Ala Lys Val Leu<br>         615                          620                      625 | 3427 |
| gag gca ata ctc aag cac ggt aac gtt gat gag gcc gta aaa ata gta<br>Glu Ala Ile Leu Lys His Gly Asn Val Asp Glu Ala Val Lys Ile Val<br>                 630                         635                      640 | 3475 |
| aag gag gtt aca gaa aaa ctc agt aaa tat gaa ata cca ccc gaa aag<br>Lys Glu Val Thr Glu Lys Leu Ser Lys Tyr Glu Ile Pro Pro Glu Lys<br>645                          650                      655 | 3523 |
| ctt gta att tat gag cag ata acg agg cct ctg agc gag tat aaa gcg<br>Leu Val Ile Tyr Glu Gln Ile Thr Arg Pro Leu Ser Glu Tyr Lys Ala | 3571 |

```
                                                                        -continued 660                    665                    670                    675
ata ggc cct cac gtt gca gta gct aaa agg ctc gca gcg aag gga gta         3619
Ile Gly Pro His Val Ala Val Ala Lys Arg Leu Ala Ala Lys Gly Val
                    680                    685                    690 aaa gtt aag cca ggg atg gtt atc ggt tac ata gtt ttg agg gga gac         3667
Lys Val Lys Pro Gly Met Val Ile Gly Tyr Ile Val Leu Arg Gly Asp
                695                    700                    705 ggg cca ata agc aag agg gcc ata gct ata gag gag ttc gat ccc aaa         3715
Gly Pro Ile Ser Lys Arg Ala Ile Ala Ile Glu Glu Phe Asp Pro Lys
            710                    715                    720 aag cat aag tac gat gcc gaa tac tac ata gag aac caa gtt ctg cca         3763
Lys His Lys Tyr Asp Ala Glu Tyr Tyr Ile Glu Asn Gln Val Leu Pro
        725                    730                    735 gcg gtg gag agg ata ttg aga gca ttt ggt tat cgc aaa gaa gat ttg         3811
Ala Val Glu Arg Ile Leu Arg Ala Phe Gly Tyr Arg Lys Glu Asp Leu
740                    745                    750                    755 agg tat caa aaa act aaa caa gtg ggc ctc gga gca tgg ctt aag ttc         3859
Arg Tyr Gln Lys Thr Lys Gln Val Gly Leu Gly Ala Trp Leu Lys Phe
                760                    765                    770 tag ctacccagat gtcaccgtat ctcaacaggt attcctggag atctcttaaa              3912
tcaactacaa gctcttcctc aagttccata aagtttattg actttatcgg tttaattatg      3972
agcttatagg agcctagaac cccagaaatc ttaactctaa agactcttga agctagctct      4032
atcagttcaa gaactatgtc cttcttaagg aacgaggaat taatgaaaac tattccttta      4092
ccgttcggat cctggagagc cattttccca actaatgtga agaagagttc gctttcaatg      4152
tagttactct cccttgtttt tagaagtctc tctaagccga cgtttatagt gaaccgtctt      4212
ttccccgtgc ttctcaaggg tagtgaaaag ttgttttctc caaactccga tatccgagcc      4272
tatttctatt ctcttcacta cgctgcccgt ttttataaat ccaccaagtt taacgaccct      4332
ggcactatct ataacatcgg tcttcagacc caatagcctt aaggtggttt ctcaaaactg      4392
agaccttccc tttagagcat tcaagaccat tagaagatca ggtctattgg ctcg             4446

<210> SEQ ID NO 2
<211> LENGTH: 771
<212> TYPE: PRT
<213> ORGANISM: archaeboacteria pyroccocus

<400> SEQUENCE: 2

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
```

-continued

```
            130                 135                 140
Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
        435                 440                 445

Phe Ile Pro Ser Leu Leu Gly Asn Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
        515                 520                 525

Leu Glu Ser Ser Gly Phe Lys Val Leu Tyr Ile Asp Thr Asp Gly Leu
    530                 535                 540

Tyr Ala Thr Ile Pro Gly Ala Lys Pro Asn Glu Ile Lys Glu Lys Ala
545                 550                 555                 560
```

```
Leu Lys Phe Val Glu Tyr Ile Asn Ser Lys Leu Pro Gly Leu Leu Glu
            565                 570                 575
Leu Glu Tyr Glu Gly Phe Tyr Ala Arg Gly Phe Phe Val Thr Lys Lys
        580                 585                 590
Lys Tyr Ala Leu Ile Asp Glu Glu Gly Lys Ile Val Thr Arg Gly Leu
        595                 600                 605
Glu Ile Val Arg Arg Asp Trp Ser Glu Ile Ala Lys Glu Thr Gln Ala
    610                 615                 620
Lys Val Leu Glu Ala Ile Leu Lys His Gly Asn Val Asp Glu Ala Val
625                 630                 635                 640
Lys Ile Val Lys Glu Val Thr Glu Lys Leu Ser Lys Tyr Glu Ile Pro
            645                 650                 655
Pro Glu Lys Leu Val Ile Tyr Glu Gln Ile Thr Arg Pro Leu Ser Glu
        660                 665                 670
Tyr Lys Ala Ile Gly Pro His Val Ala Val Ala Lys Arg Leu Ala Ala
        675                 680                 685
Lys Gly Val Lys Val Lys Pro Gly Met Val Ile Gly Tyr Ile Val Leu
    690                 695                 700
Arg Gly Asp Gly Pro Ile Ser Lys Arg Ala Ile Ala Ile Glu Glu Phe
705                 710                 715                 720
Asp Pro Lys Lys His Lys Tyr Asp Ala Glu Tyr Tyr Ile Glu Asn Gln
            725                 730                 735
Val Leu Pro Ala Val Glu Arg Ile Leu Arg Ala Phe Gly Tyr Arg Lys
        740                 745                 750
Glu Asp Leu Arg Tyr Gln Lys Thr Lys Gln Val Gly Leu Gly Ala Trp
        755                 760                 765
Leu Lys Phe
    770

<210> SEQ ID NO 3
<211> LENGTH: 2995
<212> TYPE: DNA
<213> ORGANISM: archaeobacteria Pyroccocus GE 5
<220> FEATURE:
<221> NAME/KEY: CDS
<222> LOCATION: (679)..(2991)
<221> NAME/KEY: misc_feature
<222> LOCATION: (46)..(46)
<223> OTHER INFORMATION: n is uncertain nucleotide
<221> NAME/KEY: stop codon
<222> LOCATION: (2992)..(2994)

<400> SEQUENCE: 3
tcatgtcctg gggcttggtt acggaggcta tcaaaatatt ggaccnttcg tgccagctta      60
ccagctctgg aaaatactca gtatccgcta tgtacgagat atccccaagg ctagttttta     120
atctaaagcc tatagttgtt gggtcgctgt gctgggatgg agttattatc atctcctcat     180
ttcctagcct aaacctgtcc ccaggattag gagcatggac ttcctctaat gcctccaagt     240
ggtacttgct cagggctggg gtatgatcct cgtccccata aaccacgctt ctagaaccta     300
ttagggttcc cctcttctta gtwaccccat aggtcatccc ytcaacgatc acytcggcat     360
cgttgcagtg atcggtgtgt ctatgcgaga tgaagagaac atctatcttc ctggggtcta     420
gcttatatct aatcatccta actagcgctc caggcccagg tccacaaag atattttttgc     480
ttgccttgat gaagaatcca cccgtagatc ttacttgagt tatcgtcacg aacctgcccc     540
caccggcacc caggaacgta atctctatca tttttagtcc cgaaattaaa gtgcgaggct     600
```

```
tatgctttta aggatgtatg gcgaaaggtg aagtttatta gaagttagaa tctaaagatt      660
tcagattggg tgggggta atg ata atc gat gct gat tac ata acg gaa gat        711
                   Met Ile Ile Asp Ala Asp Tyr Ile Thr Glu Asp
                    1           5                  10 ggc aag ccg ata ata agg ata ttc aaa aag gaa aag gga gag ttt aag        759
Gly Lys Pro Ile Ile Arg Ile Phe Lys Lys Glu Lys Gly Glu Phe Lys
            15                  20                  25 gta gaa tac gat agg acg ttt aga ccc tac att tat gct ctt tta aag        807
Val Glu Tyr Asp Arg Thr Phe Arg Pro Tyr Ile Tyr Ala Leu Leu Lys
        30                  35                  40 gat gat tcg gcc ata gat gag gtt aag aag ata acc gcc gag agg cac        855
Asp Asp Ser Ala Ile Asp Glu Val Lys Lys Ile Thr Ala Glu Arg His
    45                  50                  55 gga aag ata gtc agg ata acc gag gtt gag aaa gtc cag aag aaa ttc        903
Gly Lys Ile Val Arg Ile Thr Glu Val Glu Lys Val Gln Lys Lys Phe
60                  65                  70                  75 cta gga agg cca ata gaa gtc tgg aag ctc tat ctt gag cat ccc cag        951
Leu Gly Arg Pro Ile Glu Val Trp Lys Leu Tyr Leu Glu His Pro Gln
                80                  85                  90 gat gtt cca gcc ata aga gag aag ata agg gaa cat cca gct gta gtt        999
Asp Val Pro Ala Ile Arg Glu Lys Ile Arg Glu His Pro Ala Val Val
            95                  100                 105 gat ata ttt gaa tac gac ata ccc ttt gcg aag cgc tac ctc ata gac       1047
Asp Ile Phe Glu Tyr Asp Ile Pro Phe Ala Lys Arg Tyr Leu Ile Asp
        110                 115                 120 aag gga ttg act cca atg gag ggg aac gag gag cta acg ttt cta gcc       1095
Lys Gly Leu Thr Pro Met Glu Gly Asn Glu Glu Leu Thr Phe Leu Ala
    125                 130                 135 gtt gat ata gaa aca ttg tac cat gaa gga gag gag ttc ggg aaa ggg       1143
Val Asp Ile Glu Thr Leu Tyr His Glu Gly Glu Glu Phe Gly Lys Gly
140                 145                 150                 155 cca ata ata atg atc agc tac gcc gac gag gaa ggg gcc aag gtg ata       1191
Pro Ile Ile Met Ile Ser Tyr Ala Asp Glu Glu Gly Ala Lys Val Ile
                160                 165                 170 act tgg aag agc ata gac tta cct tac gtt gaa gtg gtt tcg agc gag       1239
Thr Trp Lys Ser Ile Asp Leu Pro Tyr Val Glu Val Val Ser Ser Glu
            175                 180                 185 agg gag atg ata aag agg ctc gtg aag gta att aga gag aaa gat ccc       1287
Arg Glu Met Ile Lys Arg Leu Val Lys Val Ile Arg Glu Lys Asp Pro
        190                 195                 200 gac gtg ata ata acg tac aat ggt gat aat ttc gac ttt ccg tac ctc       1335
Asp Val Ile Ile Thr Tyr Asn Gly Asp Asn Phe Asp Phe Pro Tyr Leu
    205                 210                 215 tta aag agg gct gaa aag ctc gga ata aag ctc ccc ctt gga agg gac       1383
Leu Lys Arg Ala Glu Lys Leu Gly Ile Lys Leu Pro Leu Gly Arg Asp
220                 225                 230                 235 aat agc gag ccg aaa atg cag agg atg ggg gat tca tta gcc gta gag       1431
Asn Ser Glu Pro Lys Met Gln Arg Met Gly Asp Ser Leu Ala Val Glu
                240                 245                 250 ata aag ggc aga ata cac ttc gat tta ttc ccc gcc ata aga aga acg       1479
Ile Lys Gly Arg Ile His Phe Asp Leu Phe Pro Ala Ile Arg Arg Thr
            255                 260                 265 atc aac ctt cca aca tac acc ctc gaa acg gtt tat gag gtt ata ttt       1527
Ile Asn Leu Pro Thr Tyr Thr Leu Glu Thr Val Tyr Glu Val Ile Phe
        270                 275                 280 gga aag tct aag gag aaa gtc tat gcc cat gag ata gct gag gcc tgg       1575
Gly Lys Ser Lys Glu Lys Val Tyr Ala His Glu Ile Ala Glu Ala Trp
    285                 290                 295 gaa acc ggg aaa ggg cta gag agg gta gct aag tat tca atg gaa gat       1623
```

```
                                                                -continued

Glu Thr Gly Lys Gly Leu Glu Arg Val Ala Lys Tyr Ser Met Glu Asp
300             305                 310                 315 gcg aag gta acc tct gag ctc gga aag gag ttc ttc ccg atg gaa gcc    1671
Ala Lys Val Thr Ser Glu Leu Gly Lys Glu Phe Phe Pro Met Glu Ala
            320                 325                 330 cag cta gct agg ctc gtt ggc cat cca gtt tgg gac gtt tca agg tcg    1719
Gln Leu Ala Arg Leu Val Gly His Pro Val Trp Asp Val Ser Arg Ser
        335                 340                 345 agc acc gga aac ctc gtt gag tgg ttt ctc ctt acg aag gcc tac gag    1767
Ser Thr Gly Asn Leu Val Glu Trp Phe Leu Leu Thr Lys Ala Tyr Glu
    350                 355                 360 aga aat gag ctc gcg ccc aat aaa ccg gac gag agg gaa tac gag aga    1815
Arg Asn Glu Leu Ala Pro Asn Lys Pro Asp Glu Arg Glu Tyr Glu Arg
365                 370                 375 agg cta aga gag agc tat gaa ggg ggt tac gtt aac gag cca gag aag    1863
Arg Leu Arg Glu Ser Tyr Glu Gly Gly Tyr Val Asn Glu Pro Glu Lys
380             385                 390                 395 gga ttg tgg gaa ggg ata gtc agc tta gac ttt agg tcc cta tat ccc    1911
Gly Leu Trp Glu Gly Ile Val Ser Leu Asp Phe Arg Ser Leu Tyr Pro
            400                 405                 410 tct ata att ata act cac aac gtc tca cca gac act ttg aat aga gaa    1959
Ser Ile Ile Ile Thr His Asn Val Ser Pro Asp Thr Leu Asn Arg Glu
        415                 420                 425 aat tgc aag gaa tat gac gtt gcc ccc caa gtg ggg cac aga ttc tgc    2007
Asn Cys Lys Glu Tyr Asp Val Ala Pro Gln Val Gly His Arg Phe Cys
    430                 435                 440 aag gat ttc cca gga ttc ata cca agc tta ctg ggt aac cta ctg gag    2055
Lys Asp Phe Pro Gly Phe Ile Pro Ser Leu Leu Gly Asn Leu Leu Glu
445                 450                 455 gag aga caa aag ata aaa aag agg atg aaa gaa agt aaa gat ccc gtc    2103
Glu Arg Gln Lys Ile Lys Lys Arg Met Lys Glu Ser Lys Asp Pro Val
460             465                 470                 475 gag aag aaa ctc ctt gat tac aga cag aga gct ata aaa ata ctt gca    2151
Glu Lys Lys Leu Leu Asp Tyr Arg Gln Arg Ala Ile Lys Ile Leu Ala
            480                 485                 490 aac agc tat tat ggc tat tat gga tat gca aag gcc aga tgg tac tgt    2199
Asn Ser Tyr Tyr Gly Tyr Tyr Gly Tyr Ala Lys Ala Arg Trp Tyr Cys
        495                 500                 505 aaa gag tgt gca gag agc gta acc gca tgg gga agg cag tac ata gac    2247
Lys Glu Cys Ala Glu Ser Val Thr Ala Trp Gly Arg Gln Tyr Ile Asp
    510                 515                 520 ctg gtt agg agg gaa ctt gag agc aga gga ttt aaa gtt ctc tac ata    2295
Leu Val Arg Arg Glu Leu Glu Ser Arg Gly Phe Lys Val Leu Tyr Ile
525                 530                 535 gac aca gat ggc ctc tac gca acg att cct gga gcc aag cat gag gaa    2343
Asp Thr Asp Gly Leu Tyr Ala Thr Ile Pro Gly Ala Lys His Glu Glu
540             545                 550                 555 ata aaa gag aag gca ttg aag ttc gtc gag tac ata aac tcc aag tta    2391
Ile Lys Glu Lys Ala Leu Lys Phe Val Glu Tyr Ile Asn Ser Lys Leu
            560                 565                 570 cct ggg ctt ctt gaa ttg gaa tac gaa ggt ttc tac gcg aga ggg ttc    2439
Pro Gly Leu Leu Glu Leu Glu Tyr Glu Gly Phe Tyr Ala Arg Gly Phe
        575                 580                 585 ttc gtg acg aag aaa aag tac gca cta atc gac gag gaa gga aag ata    2487
Phe Val Thr Lys Lys Lys Tyr Ala Leu Ile Asp Glu Glu Gly Lys Ile
    590                 595                 600 gtt acg agg ggg ctc gaa ata gta agg aga gat tgg agt gaa ata gca    2535
Val Thr Arg Gly Leu Glu Ile Val Arg Arg Asp Trp Ser Glu Ile Ala
605                 610                 615
```

-continued

```
aag gag acc cag gcc aag gtt ctc gag gca ata ctc aag cac ggt aac    2583
Lys Glu Thr Gln Ala Lys Val Leu Glu Ala Ile Leu Lys His Gly Asn
620                 625                 630                 635 gtt gat gag gcc gta aaa ata gta aag gag gtt aca gaa aaa ctc agt    2631
Val Asp Glu Ala Val Lys Ile Val Lys Glu Val Thr Glu Lys Leu Ser
            640                 645                 650 aaa tat gaa ata cca ccc gaa aag ctt gta att tat gag cag ata acg    2679
Lys Tyr Glu Ile Pro Pro Glu Lys Leu Val Ile Tyr Glu Gln Ile Thr
655                 660                 665 agg cct ctg agc gag tat aaa gcg ata ggc cct cac gtt gca gta gct    2727
Arg Pro Leu Ser Glu Tyr Lys Ala Ile Gly Pro His Val Ala Val Ala
        670                 675                 680 aaa agg ctc gca gcg aag gga gta aaa gtt aag cca ggg atg gtt atc    2775
Lys Arg Leu Ala Ala Lys Gly Val Lys Val Lys Pro Gly Met Val Ile
685                 690                 695 ggt tac ata gtt ttg agg gga gac ggg cca ata agc aag agg gcc ata    2823
Gly Tyr Ile Val Leu Arg Gly Asp Gly Pro Ile Ser Lys Arg Ala Ile
700                 705                 710                 715 gct ata gag gag ttc gat ccc aaa aag cat aag tac gat gcc gaa tac    2871
Ala Ile Glu Glu Phe Asp Pro Lys Lys His Lys Tyr Asp Ala Glu Tyr
            720                 725                 730 tac ata gag aac caa gtt ctg cca gcg gtg gag agg ata ttg aga gca    2919
Tyr Ile Glu Asn Gln Val Leu Pro Ala Val Glu Arg Ile Leu Arg Ala
735                 740                 745 ttt ggt tat cgc aaa gaa gat ttg agg tat caa aaa act aaa caa gtg    2967
Phe Gly Tyr Arg Lys Glu Asp Leu Arg Tyr Gln Lys Thr Lys Gln Val
        750                 755                 760 ggc ctc gga gca tgg ctt aag ttc taga                               2995
Gly Leu Gly Ala Trp Leu Lys Phe
765                 770
```

<210> SEQ ID NO 4
<211> LENGTH: 771
<212> TYPE: PRT
<213> ORGANISM: archaeobacteria Pyroccocus GE 5
<220> FEATURE:

<400> SEQUENCE: 4

```
Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
            85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160
```

-continued

```
Ser Tyr Ala Asp Glu Glu Gly Ala Lys Val Ile Thr Trp Lys Ser Ile
            165                 170                 175

Asp Leu Pro Tyr Val Glu Val Ser Ser Glu Arg Glu Met Ile Lys
            180                 185                 190

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Ala Ile Arg Arg Thr Ile Asn Leu Pro Thr
            260                 265                 270

Tyr Thr Leu Glu Thr Val Tyr Glu Val Ile Phe Gly Lys Ser Lys Glu
            275                 280                 285

Lys Val Tyr Ala His Glu Ile Ala Glu Ala Trp Glu Thr Gly Lys Gly
            290                 295                 300

Leu Glu Arg Val Ala Lys Tyr Ser Met Glu Asp Ala Lys Val Thr Ser
305                 310                 315                 320

Glu Leu Gly Lys Glu Phe Phe Pro Met Glu Ala Gln Leu Ala Arg Leu
                325                 330                 335

Val Gly His Pro Val Trp Asp Val Ser Arg Ser Ser Thr Gly Asn Leu
            340                 345                 350

Val Glu Trp Phe Leu Leu Thr Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Glu Gly Gly Tyr Val Asn Glu Pro Glu Lys Gly Leu Trp Glu Gly
385                 390                 395                 400

Ile Val Ser Leu Asp Phe Arg Ser Leu Tyr Pro Ser Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
            450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
            515                 520                 525

Leu Glu Ser Arg Gly Phe Lys Val Leu Tyr Ile Asp Thr Asp Gly Leu
            530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
```

```
                  580                 585                 590
Lys Tyr Ala Leu Ile Asp Glu Glu Gly Lys Ile Val Thr Arg Gly Leu
            595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Phe
    770

<210> SEQ ID NO 5
<211> LENGTH: 19
<212> TYPE: DNA
<213> ORGANISM: artificial  sequence
<220> FEATURE:
<221> NAME/KEY: primer
<222> LOCATION: (1)..(19)
<223> OTHER INFORMATION: Direct primer Aa

<400> SEQUENCE: 5
tccggttgat cctgccgga                                                  19

<210> SEQ ID NO 6
<211> LENGTH: 18
<212> TYPE: DNA
<213> ORGANISM: artificial sequence
<220> FEATURE:
<221> NAME/KEY: primer
<222> LOCATION: (1)..(18)
<223> OTHER INFORMATION: Reverse primer 23Sa

<400> SEQUENCE: 6
ctttcggtcg cccctact                                                   18

<210> SEQ ID NO 7
<211> LENGTH: 29
<212> TYPE: DNA
<213> ORGANISM: artificial sequence
<220> FEATURE:
<221> NAME/KEY: primer
<222> LOCATION: (1)..(29)
<223> OTHER INFORMATION: Direct primer GE23DIR

<400> SEQUENCE: 7
tggggcatat gataatcgat gctgattac                                       29
```

```
<210> SEQ ID NO 8
<211> LENGTH: 35
<212> TYPE: DNA
<213> ORGANISM: artificial sequence
<220> FEATURE:
<221> NAME/KEY: primer
<222> LOCATION: (1)..(35)
<223> OTHER INFORMATION: Reverse primer GE23REV

<400> SEQUENCE: 8
gacatcgtcg actctagaac ttaagccatg gtccg                              35

<210> SEQ ID NO 9
<211> LENGTH: 21
<212> TYPE: DNA
<213> ORGANISM: artificial sequence
<220> FEATURE:
<221> NAME/KEY: primer
<222> LOCATION: (1)..(21)
<221> NAME/KEY: primer
<222> LOCATION: (1)..(21)
<223> OTHER INFORMATION: primer Pyrococcus Sp GE5

<400> SEQUENCE: 9
tcaccttagg gttgcccata a                                             21

<210> SEQ ID NO 10
<211> LENGTH: 21
<212> TYPE: DNA
<213> ORGANISM: artificial sequence
<220> FEATURE:
<221> NAME/KEY: primer
<222> LOCATION: (1)..(21)
<221> NAME/KEY: primer
<222> LOCATION: (1)..(21)
<223> OTHER INFORMATION: primer Pyrococcus Sp. GE23

<400> SEQUENCE: 10
tgggcataaa agtcagggca g                                             21
```

US 6,673,585 B1

HEAT-STABLE DNA POLYMERASE OF ARCHAEOBACTERIA OF GENUS *PYROCOCCUS SP.*

This application is a National Stage of International Application No. PCT/FR97/01259, filed on Jul. 10, 1997, and French Application No. FR96/08631, filed on Jul. 10, 1996, both of which are incorporated herein by reference.

FIELD OF THE INVENTION

The present invention relates to new thermostable DNA polymerases derived from archaeobacteria of the genus Pyrococcus sp.

BACKGROUND OF THE INVENTION

The DNA polymerases are enzymes involved in the replication and repair of DNA. There are currently numerous known DNA polymerases isolated from microorganisms such as *E. [Escherichia] coli*; for example, DNA polymerase I of *E. coli*, the Klenow fragment of DNA polymerase I of *E. coli*, DNA polymerase T4. Thermostable DNA polymerases are also identified and purified from thermophilic organisms, such as *Thermus aquaticus* (Chien, A., et al., J. Bacteriol. 1976, 127:1550–1557; Kaladin et al., Biokhymiyay 1980, 45:644–651), *Thermus thermophilus*, or else the species bacillus (European Patent Application No. 699,760), thermococcus (European Patent Application No. 455,430), sulfobus and pyrococcus (European Patent Application No. 547,359). Among these, it is possible to mention more particularly Pfu of *Pyrococcus furiosus*, the Vent DNA polymerase of *Thermococcus litoralis* (Kong, H. M., R. B. Kucera, and W. E. Jack, 1993, J. Biol. Chem. 268(3):1965–1975), 9°-NDNA polymerase of Pyrococcus sp., 9°-N, and Deep-Vent DNA polymerase of Pyrococcus sp. GB-D.

The replication process takes place according to a well-known mechanism comprising manufacturing (from a template, DNA polymerase enzyme and four triphosphate nucleotides) a strand of complementary nucleic acid of said template. The enzymes with DNA polymerase activity are currently widely used in vitro in numerous molecular biology processes, such as cloning, detection, labeling, and amplification of nucleic acid sequences.

Amplification of nucleic acid sequences by the method called polymerase chain reaction (PCR), described in the European Patent Nos. 200,362 and 201,184, is based on the execution of successive cycles of extensions of primers, using a DNA polymerase and the four triphosphate nucleotides, followed by denaturation of the double-strand nucleic acids thus obtained and used as templates for the next cycle. Since the temperatures used in the denaturation step are not compatible with preservation of the activities of numerous DNA polymerases, important research studies are dedicated to the thermostable enzymes described in the preceding. It is particularly essential not to limit the preparation of these enzymes solely to the processes of purification from microorganisms, but to seek to increase the production yields using methods of genetic engineering. According to these methods, which are well known to the experts in the field (Maniatis et al., Molecular Cloning: A Laboratory Manual, 1982), the gene coding for DNA polymerase is cloned in an expression vector, a vector which is inserted in a cellular host capable of expressing the enzyme, the cellular host is grown under suitable conditions, and the DNA polymerase is isolated and recovered. This method was described, for example, in the patent application PCT WO89/06691 for producing DNA polymerase of *Thermus aquaticus*.

SUMMARY OF THE INVENTION

The present invention relates to thermostable purified DNA polymerase of archaeobacteria of the genus Pyrococcus sp.

Figure 1:
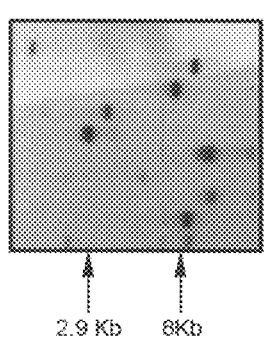
FIG. 1 shows a Southern blot analysis revealing an 8-kb XbaI—XbaI positive fragment using probe PfuF.

The development of recombinant DNA technologies in the field of research as well as in that of industrial production requires one to have various DNA polymerases capable of improving quantitatively or qualitatively, techniques as diverse as cloning, detection, labeling, or amplification of nucleic acid sequences.

The present invention aims precisely to offer new hyperthermostable enzymes obtained from Pyrococcus sp. species which catalyze the polymerization of DNA. These enzymes come from isolates of samples of hyperthermophilic archaeobacteria (Woese, C. R., O. Kandler, and M. Wheelis, 1990, Proc. Natl. Acad. Sci. USA 87:4576–4579) taken from deep hydrothermal springs of the North-Fiji basin in the south Pacific (Desbruyeres, D., A.-M. Alayse-Danet, and S. Ohta, 1994, Geology 116:227–242; Marteinsson, V. T., L. Watrin, D. Prieur, J. C. Caprais, G. Raguenes, and G. Erauso, 1995, International Journal of Systematic Bacteriology 45(4):623–632). All these isolates are hyperthermostable with isolation temperatures on the order of 80 to 100° C. A DNA polymerase of the invention has a molecular weight of approximately 89,000 d and has a hyperthermostability which enables it to be used in reactions conducted at temperatures of 70–90° C.

The studies performed in the context of the invention made it possible to identify two new thermostable DNA polymerases of archaeobacteria of the genus Pyrococcus sp. whose phylogenetic relationship was studied. The genes coding for these two DNA polymerases were cloned and sequenced, and their comparison revealed great similarities of sequence and organization.

The invention relates more particularly to a thermostable purified DNA polymerase of archaeobacteria of the genus Pyrococcus sp. which has a molecular weight between approximately 89,000 and 90,000 d.

A first thermostable purified DNA polymerase according to the invention comes from the strain of archaeobacteria of the genus Pyrococcus sp. filed in the National Microorganism Culture Collection (CNCM) at the Pasteur Institute, Jul. 3, 1996 under the No. I-1764. This DNA polymerase will subsequently be called Pyrococcus sp. GE 23. Its sequence of 771 amino acids is represented in the appended sequence list under the number SEQ ID NO:2. A molecular weight of 89,409 d and a pI of 8.37 were deduced from this sequence. The invention relates then to the DNA polymerase of Pyrococcus sp. GE 23 whose amino acid sequence is represented in the appended sequence list under the number SEQ ID NO:1 or any other sequence constituting a derivative which is enzymatically equivalent to it. Enzymatically equivalent derivatives are understood to mean the polypeptides and proteins comprising or including the amino acid sequence represented in the appended sequence list under the number SEQ ID NO:2 when they have the properties of the DNA polymerase of Pyrococcus sp. GE 23. On this basis, the invention more particularly envisages a DNA polymerase whose amino acid sequence is a fragment of that represented in the appended sequence list under the number SEQ ID NO:2 or else an assemblage of such fragments.

Enzymatically equivalent derivatives are also understood to mean the amino acid sequences above modified by insertion and/or deletion and/or substitution of one or more amino acids, in as much as the resulting properties of the DNA polymerase of Pyrococcus sp. GE 23 are not significantly modified.

A second thermostable purified DNA polymerase according to the invention comes from the strain of archaeobacteria of the genus Pyrococcus sp. filed in the CNCM, Apr. 20, 1993 under the No. I-1302. This DNA polymerase will subsequently be called Pyrococcus sp. GE 5 (otherwise known as *Pyrococcus abyssi*). Its sequence of 771 amino acids is represented in the appended sequence list under the number SEQ ID NO:4. A molecular weight of 89,443 d and a pI of 8.13 were deduced from this sequence.

The invention relates then to the DNA polymerase of Pyrococcus sp. GE 5 whose amino acid sequence is represented in the appended sequence list under the number SEQ ID NO:4 or any other sequence constituting a derivative which is enzymatically equivalent to it. Enzymatically equivalent derivatives are understood to mean the polypeptides and proteins comprising or including the amino acid sequence represented in the appended sequence list under the number SEQ ID NO:4 when they have the properties of the DNA polymerase of Pyrococcus sp. GE 5. On this basis, the invention more particularly envisages a DNA polymerase whose amino acid sequence is a fragment of that represented in the appended sequence list under the number SEQ ID NO:4 or else an assemblage of such fragments.

Enzymatically equivalent derivatives are also understood to mean the amino acid sequences above modified by insertion and/or deletion and/or substitution of one or more amino acids, in as much as the resulting properties of the DNA polymerase of Pyrococcus sp. GE 5 are not significantly modified.

The DNA polymerases of Pyrococcus sp. GE 23 and of Pyrococcus sp. GE 5 are distinguished from one another by 10 amino acid residues whose positions are indicated in Table I below.

TABLE 1

| Positions | Pyrococcus sp. GE 23 | Pyrococcus sp. GE 5 |
|---|---|---|
| 263 | Val | Ala |
| 277 | Ala | Thr |
| 281 | Ala | Val |
| 320 | Phe | Ser |
| 339 | Gln | His |
| 359 | Arg | Thr |
| 391 | Lys | Asn |
| 532 | Ser | Arg |
| 553 | Pro | His |
| 554 | Asn | Glu |

The invention also relates to a DNA sequence comprising the sequence coding for a thermostable purified DNA polymerase according to the invention.

A first DNA sequence according to the invention comprises the nucleotides 1547 to 3862 of SEQ ID NO:1 coding for the 771 amino acids of the DNA polymerase of Pyrococcus sp. GE 23.

A second DNA sequence according to the invention comprises the nucleotides 678 to 2994 of SEQ ID NO:3 coding for the 771 amino acids of the DNA polymerase of Pyrococcus sp. GE 5.

The invention relates as much to the thermostable DNA polymerase defined in the preceding isolated and purified from a strain of Pyrococcus sp. as to the thermostable DNA polymerase prepared by the methods of genetic engineering. Consequently, the invention also relates to a vector which includes a DNA sequence defined in the preceding, as well as to a process for production or expression in a cellular host of the thermostable DNA polymerases of the invention.

A process for production of a thermostable DNA polymerase according to the invention comprises:

of transferring a molecule of nucleic acid coding for a thermostable DNA polymerase or a vector containing said molecule into a cellular host, of growing the cellular host obtained in the preceding step under conditions making possible the production of the DNA polymerase, of isolating said DNA polymerase by any suitable means.

The cellular host used in the preceding processes can be chosen from the prokaryotes or the eukaryotes and particularly from bacteria, yeasts, and from cells of mammals, plants or insects.

The vector used is chosen as a function of the host into which it will be transferred; it can be any vector such as a plasmid.

The thermostable DNA polymerases of the invention can be used particularly in processes of enzymatic amplification of nucleic acid sequences. Consequently, the invention relates to such processes using a thermostable DNA polymerase described in the preceding as well as to the amplification kits which contain a suitable quantity of this DNA polymerase besides the reagents which are generally used.

Other advantages and characteristics of the invention will appear upon reading of the following examples given on a nonlimiting basis and relating to the cloning, expression, characterization, and activity of the thermostable DNA polymerases of the invention.

I Materials and Methods

1) Culture Conditions, Plasmids, and Strains Used

The strains Pyrococcus furiosus (DSM 5262) and Thermococcus litoralis (DSM 5474) were obtained from the collection of the German Collection of Microorganisms (DSM) Braunschweig—Stocheim, Germany. The strains Pyrococcus sp. G 23 and G 5 were isolated from vents of deep hydrothermal springs discovered in the Starmer Franco-Japanese campaign occurring in 1989 at 2000 m depth in the North-Fiji basin.

Pyrococcus sp. G 5 was grown anaerobically in an 8-L fermenter in BHI medium (Difco) supplemented with sulfur at a pH of 6.5 and at 90° C., as described in the literature (Erauso, G., A. L. Reysenbach, A. Godfroy, J.-R. Meunier, B. Crump, F. Partensky, J. A. Baross, V. Marteinsson, G. Barbier, N. R. Pace and D. Prieur, 1993, Arch. Microbiol. 160:338–349).

Pyrococcus sp. G 23 was grown at 85° C. in an identical fermenter in 2216S medium (Difco) at a pH of 6.5.

The strain E. coli SURE, XL-1-Blue (Stratagene, LaJolla, Calif. USA) was used as host for the recombinant plasmids from pUC18 and pBluescript. The strains E. coli NOVABLUE, BL21(DE3), and BL21(DE3)pLysS (Novagen, Madison, Wis. USA) were used as hosts for the derived recombinant plasmids. E. coli SURE, XL1-Blue, NOVABLUE, BL21(DE3), and BL21(DE3)pLysS were grown,in LB medium (Difco) or LB medium (Difco) supplemented with appropriate antibiotics.

2) Isolation of the DNA, Hybridization, and Recombinant DNA

The high-molecular-weight DNA of Pyrococcus sp. G 23 and G 5 was isolated by the modified Charbonnier method (Charbonnier, F., G. Erauso, T. Barbeyron, D. Prieur, and P. Forterre, 1992, J. Bacteriol. 174(19):6103–6109). The centrifuged cells were resuspended in TE-Na-1×buffer, then lysed at 40° C. for 3 h with a mixture of N-lauryl sarcosine 1%, sodium dodecyl sulfate 1% and 0.4 mg/mL of proteinase K. After centrifugation at 5000 G for 10 min, the DNA is extracted by PCI (25-24-1), and then treated with RNAase at a concentration of 5 μg/mL at 60° C. for 1 h. These steps are followed by an additional extraction with PCI and chloroform extraction. The DNA is precipitated with 100% ethanol, and the pellets are dried and suspended in TE-1×. The concentration and purity of the DNA were estimated by spectrophotometry at 230, 260, and 280 nm with a GeneQuantII apparatus (Pharmacia, Upsalla, Sweden). For the construction of the pUC18 minilibrary (Sutherland, K. J., C. M. Henneke, P. Towner, and D. W. Hough, 1990, European J. Biochem., 194:839–844) of Pyrococcus sp. G 23, the genomic DNA was digested by a series of restriction enzymes (BamHI, Bg[1]II, EcoRI, EcoRV, HindIII, PvuII, SalI, SacI, XbaI, and XhoI) by single or double digestion. Then, the DNA fragments underwent a migration on 0.8% agarose gel in TBE-1× and were transferred onto Hybond-N+nylon membrane (Amersham, UK) and hybridized with DNA probes prepared by PCR with specific primers selected from genes of DNA polymerase of P. furiosus and T. litoralis, labeled with $^{32}P$ by random-priming according to the recommendations of the manufacturer (Magaprime, Amersham, UK). Two probes of P. furiosus were used, pFuΣ and PfuF, respectively covering the regions delimited by the base pairs 8-2316 and 819-1915 of the coding region of the polymerase Pfu gene, as defined by Uemori et al. (Uemori, T., Y. Ishino, H. Toh, K. Asada, and I. Kato, 1993, Nucleic Acids Res. 21(2):259–265). Two probes of T. litoralis were used, TliI and TliT, respectively covering the regions delimited by the base pairs 297-1768 and 4631-5378, as defined by Hodges et al. (Hodges, R. A., F. B. Perler, C. J. Noren, and W. E. Jack, 1992, Nucleic Acids Res. 20(23):6153–6157). The positive fragments, identified by DNA—DNA hybridization (Southern, E. M., 1975, Journal of Molecular Biology, 98:503), were then prepared by appropriate digestions of 100 μg of genomic DNA, purified using agarose gels in dialysis bags, and precipitated with 100% ethanol. The fragments were ligated in pUC18, which had been cut by appropriate restriction enzymes for a single and dephosphorylated digestion. The transformation of the host strains was done by electroporation (Gene Pulser, Biorad). The screening of the recombinant clones was done by colony hybridization according to the techniques described in the literature (Sambrook, J., E. F. Fritsch, and T. Maniatis, 1989, Molecular Cloning: A Laboratory Manual, 2nd ed. Cold Spring Harbor Laboratory Press, Cold Spring Harbor). The temperature of the Southern blots and of colony hybridization was 55° C. in a standard buffer without formamide. The plasmid DNA was isolated by the method of Bimboim and Doly (Bimboim, H. C., and J. Doly, 1979, Nucleic Acids Res., 7:1503), then purified by solid-phase anion-exchange chromatography (Quiagen, Chatsworth, Calif. USA). The restriction fragments of the plasmids derived from pUC were purified using agarose gels by the GeneClean method (Bio 101, LaJolla, Calif.) for later cloning. The polymerization chain reactions (PCR) of long fragments were carried out according to the procedure defined by Barnes (Barnes, W. M., 1994, Proc. Natl. Acad. Sci. USA 91:2216–2220) with a Taq Extender reaction mixture (Stratagene, LaJolla, Calif.). The rDNA of 16S and 23S of Pyrococcus sp. GE 23 were amplified by PCR with a Stratagene 96-well thermocycler using the following conditions:

direct primer Aa (5'-TCCGGTTGATCCTGCCGGA-3') (SEQ ID NO:5),
indirect primer 23Sa (5'-CTTTCGGTCGCCCCTACT-3') (SEQ ID NO:6),
initial step 3 min at 94° C. followed by 30 cycles (94° C., 1 min/49° C., 1 min/72° C., 2 min) and,
final elongation of 5 min at 72° C.

The PCR products were cloned in the vector pBluescript for sequencing.

The gene of the DNA polymerase of Pyrococcus sp. GE 5 was isolated by PCR using the primers developed for expressing the gene of the DNA polymerase of Pyrococcus sp. GE 23:

5'-TGGGGCATATGATAATCGATGCTGATTAC-3' (SEQ ID NO:7)
5'-GACATCGTCGACTCTAGAACTTAAGCCATGGT-CCG-3'(SEQ ID NO:8)

3) Sequencing of the DNA

The DNA sequences were obtained by the dideoxy chain termination method (Sanger, F., S. Nicklen, and A. R. Coulson, 1977, Proc. Natl. Acad. Sci. USA 74:5467–5473) using an Applied Biosystems automatic DNA analysis system. The two strands of the genes coding for the DNA polymerase of Pyrococcus sp. G 23 and G 5 were sequenced, while the 16S rDNA of Pyrococcus sp. G 23 was sequenced on a single strand, using universal primers located on vectors and internal primers.

The sequence analysis was done with DNASTAR software (Madison, Wis., USA), and the Genetics Computer Group program (University of Wisconsin Biotechnology Center, Madison, Wis., USA) which is accessible on-line using INFOBIOGEN. The computerized similarity searches were done with the BLAST program, the multiple alignments with CLUSTAL V, and the phylogenetic trees were established according to the method called "neighbor-joining" (Saitou, N. and M. Nei, 1987, Mol. Biol. Evol. 4(4):406–425).

4) Construction of the Recombinants Expressing the DNA Polymerase of Pyrococcus sp. G 23 and G 5

The DNA polymerases of Pyrococcus sp. G 23 and G 5 were expressed in *E. coli* using the pET12 expression system, belonging to the T7 expression system (Studier, F. W., A. H. Rosenberg, F. J. Dunn, and J. W. Dubendorff, 1990, Methods Enzymol. 185:60–89) purchased from Novagen (Madison, Wis., USA). PCR was used to prepare the fragments of Pyrococcus sp. G 23 and G 5 containing the restriction sites NdeI and SalI which are compatible with the ends of primers GE23DIR and GE23REV. The PCR mixture contained Goldstar DNA polymerase (Eurogentec, B), the *Taq*-extended *Taq* enzyme (Pfu of Stratagene), the extension buffer with the four dNTP (each at 0.2 mM) and the primers GE23DIR and GE23REV at a concentration of 50 pmol in a final volume of 50 µL. The amplification was done over 20 cycles: 1 min at 90° C., 1 min at 50° C. and 3 min at 72° C., using a Stratagene 96-well thermocycler. The PCR fragments digested by NdeI and SalI were ligated to the sites NdeI and SalI of pET12a which were digested by the same enzymes, thus reestablishing the initiation codon. The constructions obtained were respectively named pETPAB1 and pETGE1. These constructions were both sequenced at the junction sites and entirely in the case of pETPAB1. The expression tests were carried out according to the recommendations of the manufacturer of the pET expression system: Selection of the clones in *E. coli* Novablue, culture of *E. coli* BL21(DE3), induction (IPTG 0.2–1 mM).

750 µL of cells of $OD_{600}$=1 induced and noninduced cultures were centrifuged, resuspended in lysis buffer B (Tris HCl 10 mM pH 7.5; NaCl 10 mM; $MgCl_2$ 2 mM; Triton X-100 1% vol/vol). The DNA polymerase was observed by SDS-PAGE after a partial thermal denaturation of the host proteins (71° C., 20 min) and concentrated using Millipore filters (Ultrafree MC). The activity was tested by measurement of the incorporation of $^3$H-dTTP (Amersham, UK) using activated calf thymus DNA as substrate (Sigma-Aldrich, F) in reaction medium C (Tris HCl 50 mM pH 8.8; DTT 1 mM; $MgCl_2$ 10 mM; KCl 10 mM; BSA 0.4 mg/mL, each dNTP at 0.4 mM).

II Results

1) Isolation of the Gene of the DNA Polymerase of Pyrococcus sp. GE 23

Figure 2:
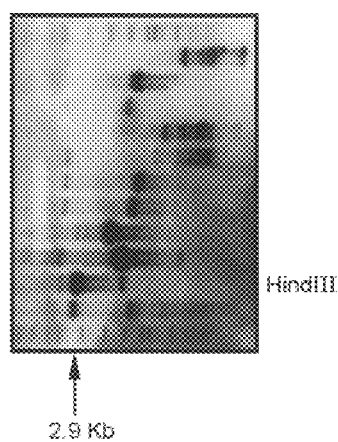
FIG. 2 shows a Southern blot analysis revealing a 2.9-kb HindIII—HindIII positive fragment using a TliI probe labeled with $^{32}$P.

The genomic DNAs of the strains Pyrococcus sp. GE 23 and GE 5, digested by a series of restriction enzymes, were hybridized with the DNA of *P. furiosus* and with probes of *T. litoralis* prepared by PCR. As shown in FIGS. 1 and 2, the Southern blot analyses revealed a 2.9-kb HindIII—HindIII positive fragment with a TliI probe labeled with $^{32}$P (FIG. 2), whereas probe PfuF revealed an 8-kb XbaI—XbaI positive fragment (FIG. 1) (24-h exposure). The 2.9-kb fragment was isolated and purified as described in the preceding Materials and Methods section and cloned into the vector pUC18 digested by HindIII. Approximately 600 recombinants (*E. coli* SURE) were screened with a radioactively labeled TliI probe, and 6 of them gave a positive hybridization signal. Identical restriction profiles were obtained for these clones, indicating that they probably contained the same insert. The later sequencing of one of these clones (designated pGE23a) and the sequence comparison (FASTA) demonstrated that it corresponds to the first 1358 base pairs of the gene of the DNA polymerase belonging to family B (Braithwaite, D. K., and J. Ito, 1993, Nucleic Acids Res. 21(4):787–802) and that it ends with the HindIII site. The analysis of the nucleotide sequence shows that the XbaI site is located upstream from the initiation codon and that consequently, the 8-kb XbaI—XbaI positive fragment should contain the 3' part of the gene. According to the same method, this 8-kb fragment was cloned into vector pUC18, and 3 positive recombinant clones out of 800 were identified by colony hybridization as in the preceding using a homologous probe prepared from the 5' part of the gene of the DNA polymerase of Pyrococcus sp. GE 23. The cultures of these clones in a liquid medium (LB-ampicillin) were systematically lysed well before $OD_{600}$=0.5. One culture was stopped at $OD_{600}$=0.1, and the plasmid DNA (designated pGE23b) was extracted. The long distance PCR (with the *Taq* Extender) was performed on this plasmid DNA using a direct primer located on the 5' part of the sequence obtained in the preceding and a reverse primer located downstream on the vector pUC18, in order to obtain an 8-kb amplification product. The 3' part was sequenced later. Then, another long distance PCR was done using the same direct primer located on the 5' part of the gene and a reverse primer located on the available 3' part. The amplification products of 10 separate PCR reactions were collected, purified by electrophoresis using agarose gel and sequenced on the two strands using internal primers. These products contain the 3' part of the gene of the DNA polymerase of Pyrococcus sp G 23.

2) Phylogenetic Position of Pyrococcus sp. G 23 and G 5

Figure 3:
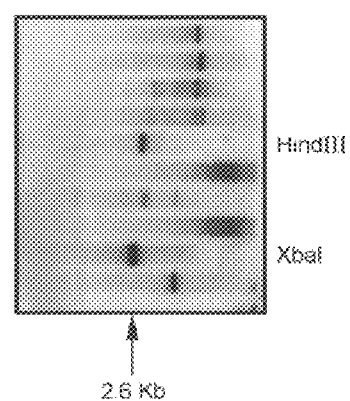
FIG. 3 shows the different RFLP profiles of the genes of DNA polymerase of Pyrococcus sp. G 23 and G 5, obtained with the different probes (pFuΣ, PfuP, TliI).
Figure 4:
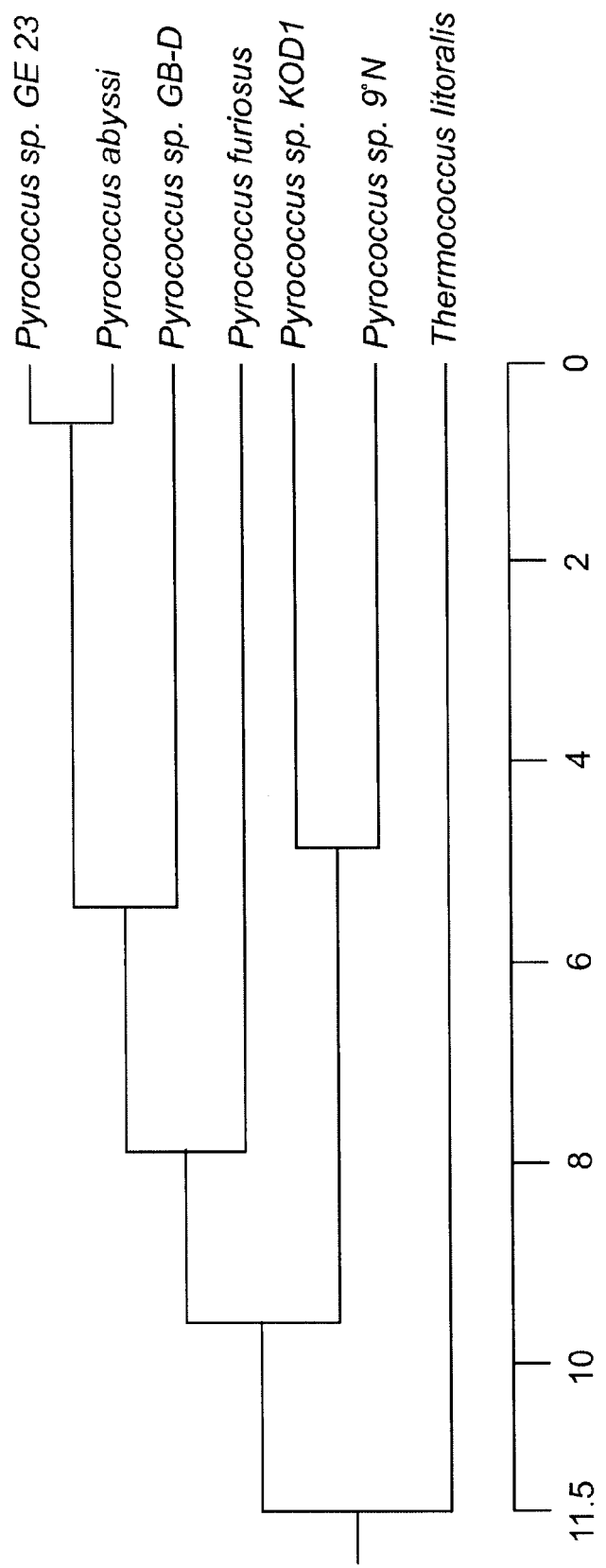
FIG. 4 shows the phylogenetic tree of the DNA polymerases of Thermococcales.
Figure 5:
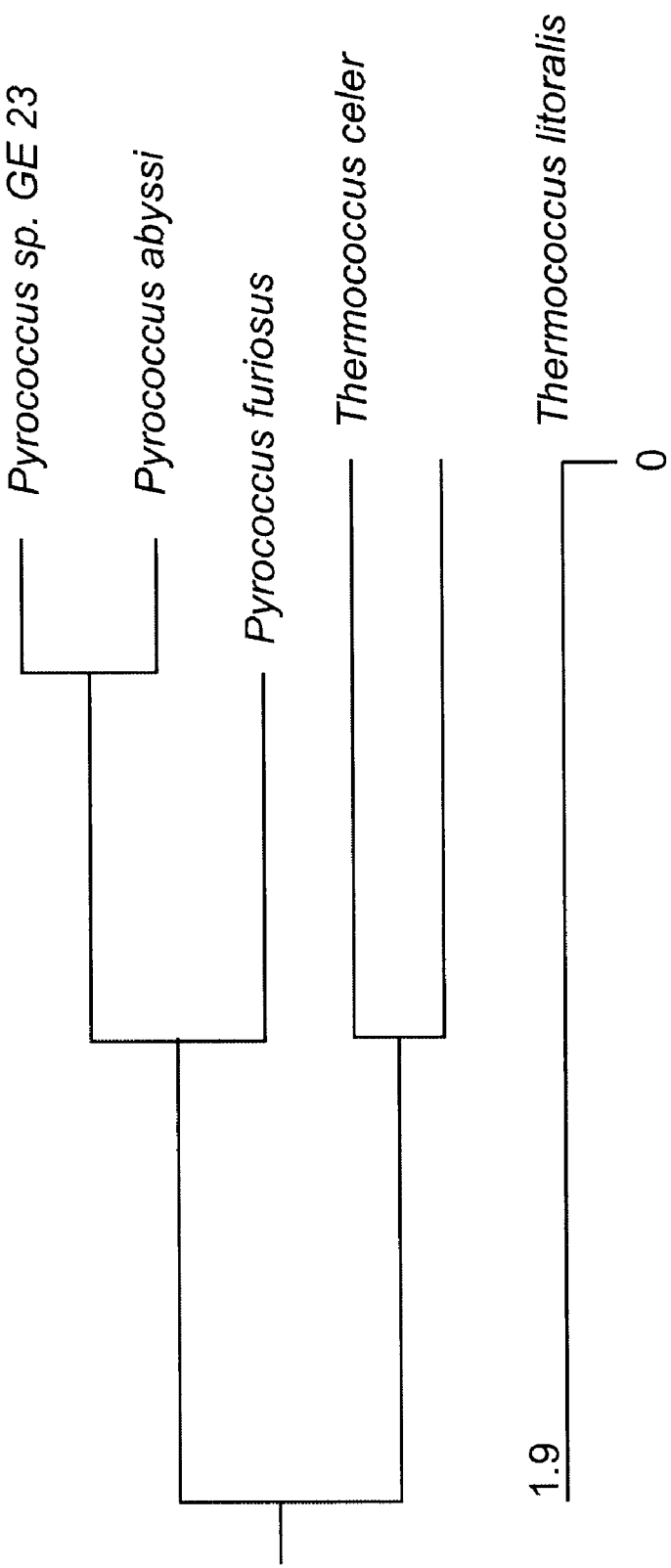
FIG. 5 shows the phylogenetic situation of Pyrococcus sp. G 23 and Pyrococcus sp. GE 5 (*Pyrococcus abyssi*) based on the 16S rDNA sequences.

Pyrococcus sp. G 23 and G 5 belong to the same 16S rDNA PCR-RFLP group (Meunier, J. R., 1994, Biodiversity and systematics of populations of thermophilic microorganisms isolated from abyssal oceanic hydrothermal ecosystems. Thesis, Paris 7), indicating that they could be two different strains of the same species. However, as shown in FIG. 3, the different RFLP profiles of the genes of DNA polymerase of Pyrococcus sp. G 23 and G 5, obtained with the different probes (pFuΣ, PfuP, TliI) indicate that at least the genes of the DNA polymerase have significant differences. Slot blot DNA-DNA hybridizations (Marteinsson, V. T., L. Watrin, D. Prieur, J. C. Caprais, G. Raguenes, and G. Erauso, 1995, Int. J. Systemat. Bacteriol. 45(4):623–632) led to contradictory relationship levels: 79% between unlabeled GE 23 and labeled GE 5, and 98% between unlabeled GE 5 and labeled GE 23. The amplification of the genes of the 16S–23S rDNA was done as described in the preceding in Materials and methods. The 1.9-kb amplified band was purified and sequenced on one strand. The complete 16S rDNA sequence was compared with its counterpart of Pyrococcus sp. GE 5 and of other species of Pyrococcus sp. and thermococcus. The level of similarity between Pyrococcus sp. GE 23 and Pyrococcus sp. GE 5 is 97.8%, and Pyrococcus sp. GE 23 was regrouped with Pyrococcus sp. GE 5 (*Pyrococcus abyssi*) in the phylogenetic tree of the DNA polymerases of Thermococcales of FIG. 4. Likewise, FIG. 5 represents the phylogenetic situation of Pyrococcus sp. G 23 and Pyrococcus sp. GE 5 (*Pyrococcus abyssi*) based on the 16S rDNA sequences. In these two figures, the dendrogram was established by the "neighbor-joining" method, and the scale represents the relative distance between the sequences.

3) Identification of the Gene of the DNA Polymerase of Pyrococcus sp. GE 5

Deducing from the relationship between these two strains that the direct isolation of the gene of the DNA polymerase of Pyrococcus sp. GE 5 was possible by PCR, the two primers GE23DIR and GE23REV, prepared for cloning the gene of the DNA polymerase of Pyrococcus sp. GE 23 in the vector pET12, were used in a PCR reaction containing the genomic DNA of Pyrococcus sp. GE 5. The amplification products of 5 PCR reactions were collected, purified; and sequenced on the two strands. The nucleotide sequence has a strong homology (97%) with the gene of the DNA polymerase of Pyrococcus sp. GE 23. In order to obtain the sequence of the gene of the DNA polymerase of Pyrococcus sp. GE 5, different cloning tests were done. First of all, a 2.9-kb HindIII—HindIII fragment, identified by DNA—DNA hybridization, as shown in FIG. 3, was cloned into the vector pUC18, transformed into *E. coli* SURE and sequenced. It shows itself to be homologous to the 2.9-kb HindIII—HindIII fragment of Pyrococcus sp. GE 23 cloned in the preceding and containing the 5' part of the target gene. Secondly, a 2.6-kb XbaI—XbaI positive fragment, potentially containing all of the coding region, was identified by DNA—DNA hybridization using the gene of the DNA polymerase of Pyrococcus sp. GE 5 produced by PCR as a radio labeled probe. This fragment was cloned in the vectors pUC18, pBluescript, and pET12 and transformed in *E. coli* Novablue (strain recA⁻). Three positive recombinant clones out of 600 were obtained with pET12 and none were obtained with pUC18 and pBluescript. The restriction profiles of the pET12 recombinant clones demonstrate that the integrity of the construction was not preserved. FIG. 3 shows that the major part of the insert was deleted in the process, and only the 342-bp HindIII-XbaI 3' fragment remains. The definitive sequence of the gene of the DNA polymerase of Pyrococcus sp. GE 5 is composed of an HindIII—HindIII genomic 5' part, a 611-bp HindIII—HindIII internal region coming from PCR products, and the genomic 342-bp 3' part.

4) Nucleotide and Polypeptide Sequences of the DNA Polymerases of Pyrococcus sp. GE 23 and GE 5.

a) DNA Polymerase of Pyrococcus sp. GE 23

The 2.9-kb HindIII—HindIII Pyrococcus sp. GE 23 fragment which was cloned, as well as a contiguous 1.6-kb fragment in the 3' direction obtained by long distance PCR, were sequenced on the two strands and assembled. The 4447-bp sequence obtained was studied in order to determine the regions capable of being translated. Two open reading frames were revealed. The first, in frame 2, extending from the base pair 1547 to the base pair 3862, corresponds to the gene of the DNA polymerase coding for a protein with 771 amino acids, whose molecular weight deduced from the sequence is 89,409 D and whose theoretical isoelectric point is 8.37. This molecular weight corresponds to the apparent molecular weight estimated by SDS-PAGE of the recombinant DNA polymerase. The second ORF was located on frame 4 between the base pairs 1439 and 627.

The deduced sequence has a length of 270 amino acids and the similarity searches done with the programs BLAST and FASTA did not reveal any significant homology with the available sequences in the Swiss-Prot and PIR databases.

b) DNA Polymerase of Pyrococcus sp. GE 5

The complete coding sequence of the gene of the DNA polymerase of Pyrococcus sp. GE 5 produced by PCR using the primers prepared from the gene of Pyrococcus sp. GE 23 was obtained by sequencing the two strands. In order to confirm the sequence of this PCR product, the 2.9-kb HindIII—HindIII Pyrococcus sp. GE 5 fragment cloned was also sequenced on the two strands, and the same results were obtained. The 3' region of the gene was also sequenced from the remaining 342-bp HindIII-XbaI insert resulting from the deletion of a part of the 2.6-kb XbaI—XbaI fragment. Only the 611-bp HindIII—HindIII internal region of the sequence of the gene obtained from the PCR products could not be confirmed at the genomic level. An open reading frame between base pairs 679 and 2994 was identified, whose translation produces a polypeptide sequence of 771 amino acids, length which is identical to that of the DNA polymerase of Pyrococcus sp. GE 23.

c) Comparison of the Sequences of the Two Polymerases

The alignment of the coding regions of the two genes shows their strong relationship since they only differ by 64 nucleotides dispersed along the sequences with two exceptions. First of all, one observes 14 substitutions between base pairs 1541 and 1603, making this region the most variable of the whole sequence; then one observes a limited number of substitutions in the 3' region between base pairs 1890 and 2316. The majority of these substitutions have no consequence with regard to the polypeptide sequences; particularly the first 23 substitutions have no effect on the protein composition. The comparison with other genes of DNA polymerases of thermococcales which are available in the databases reveal that the highly variable region between base pairs 1541 and 1603 of Pyrococcus sp. GE 23 and GE 5 seems to be a characteristic of these two strains, the diversity being well distributed over the other sequences of genes coding for DNA polymerases. The comparison with regard to the polypeptide sequences shows the great similarity of the two DNA polymerases, 98% homology with the CLUSTAL V method, and only 10 different residues. The amino acid substitutions are given in Table I.

Table II below indicates the percentage of similarities between the polypeptide sequences of:
(1) Pyrococcus sp. GE 23, (2) Pyrococcus sp. GE 5,
(3) Pyrococcus sp. GB-D, (4) Pyrococcus sp. KOD1,
(5) *Pyrococcus furiosus*, (6) *Thermococcus litoralis*,
(7) Pyrococcus sp. 9° N.

TABLE II

| (1) | (2) | (3) | (4) | (5) | (6) | (7) | |
|---|---|---|---|---|---|---|---|
| *** | 98,6 | 89,2 | 81,3 | 83,5 | 76,3 | 81,5 | (1) |
|  | *** | 88,4 | 80,6 | 82,8 | 75,5 | 80,9 | (2) |
|  |  | *** | 81,6 | 85,1 | 77,1 | 83,0 | (3) |
|  |  |  | *** | 79,2 | 78,1 | 90,4 | (4) |
|  |  |  |  | *** | 74,0 | 80,1 | (5) |
|  |  |  |  |  | *** | 77,0 | (6) |
|  |  |  |  |  |  | *** | (7) |

The majority of the amino acid substitutions between the DNA polymerases of Pyrococcus sp. GE 23 and GE 5 are nonconserved, but none is located in units known to be involved in the catalytic action of the enzyme, or in the exonuclease or polymerase 3'-5' domains. The two genes have no intron sequence (IVS or inteines) contrary to the genes of DNA polymerase of *T. litoralis*, Thermococcus sp. KOD1, Pyrococcus sp. GG-D, and have the same organization as the genes of DNA polymerase of *P. furiosus* and Pyrococcus sp. 9° N.

5) Expression, Characterization, and Activity of the DNA Polymerase of Pyrococcus sp. GE 5 a) Cloning and Expression

A 2320-bp insert covering the 2316-bp DNA sequence of SEQ ID NO:1 coding for the DNA polymerase of Pyrococcus sp. GE 5 was cloned at the sites NdeI and BamHI of a vector in order to transform the *E. coli* strain BL21(DE3). Minipreparations of plasmid DNA were produced using approximately twenty transforming clones, and a single one was selected based on the size of the DNA fragments released after digestion by the NdeI and BamHI restriction enzymes.

Figure 6:
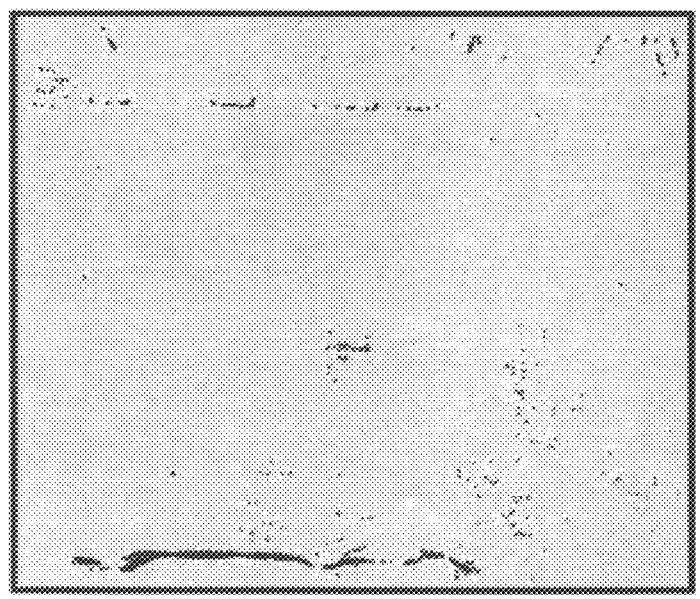
FIG. 6 represents the results of the expression tests, in which: Well No. 1 corresponds to the 10-kDA Ladder protein (Gibco BRL); Well No. 2 corresponds to the sample induced without IPTG, time 0 (exponential growth phase); Well No. 3 corresponds to the sample induced without IPTG, 1 h after induction; Well No. 4 corresponds to the sample induced without IPTG, 4 h after induction; Well No. 5 corresponds to the sample induced without IPTG, 18 h after induction; Well No. 6 corresponds to the 10-kd ladder protein (Gibco BRL); Well No. 7 corresponds to the sample induced with 1 mM IPTG, time 0 (exponential growth phase); Well No. 8 corresponds to the sample induced with 1 mM IPTG, 1 h after induction; Well No. 9 corresponds to the sample induced with 1 mM IPTG, 4 h after induction; and Well No. 10 corresponds to the sample induced with 1 mM IPTG, 18 h after induction.

Expression tests were then done at 37° C., in Erlenmeyer flasks, with the selected clone. The expression is induced in exponential growth phase (OD 600 nm=0.6–0.7) with IPTG concentrations of 0, 0.5, 1, and 1.5 mM. Samples are removed at different times in the course of the culture, and the proteins are analyzed by electrophoresis using acrylamide gel and with Coomassie blue. FIG. 6 represents the results of the expression tests, in which:

Well No. 1 corresponds to the 10-kDA Ladder protein (Gibco BRL).

Well No. 2 corresponds to the sample induced without IPTG, time 0 (exponential growth phase).

Well No. 3 corresponds to the sample induced without IPTG, 1 h after induction.

Well No. 4 corresponds to the sample induced without IPTG, 4 h after induction.

Well No. 5 corresponds to the sample induced without IPTG, 18 h after induction.

Well No. 6 corresponds to the 10-kd ladder protein (Gibco BRL).

Well No. 7 corresponds to the sample induced with 1 mM IPTG, time 0 (exponential growth phase).

Well No. 8 corresponds to the sample induced with 1 mM IPTG, 1 h after induction.

Well No. 9 corresponds to the sample induced with 1 mM IPTG, 4 h after induction.

Well No. 10 corresponds to the sample induced with 1 mM IPTG, 18 h after induction.

One observes that only the cells grown in the absence of IPTG express the DNA polymerase, and the level is maximum after a night of culture. The molecular weight of the expressed protein is estimated at 89 kd.

b) Fermentation and Extraction of the Cells

The culturing of the strain Pyrococcus sp. GE 5 was done according to a standard protocol. One added the selection factor for the plasmid to the R12 medium chosen for the preculture and the culture. The transfer of the preculture to the fermenter was done when the optical density at 600 nm of the preculture was approximately 0.8. The NBS MICROS fermenter (25 L) was used for this production, with a culture volume of 24 L. The fermentation conditions were as follows: Temperature=37° C.; shaking=300 rpm; aeration=30 L/m; dissolved oxygen=15%. The pH was adjusted to 6.8 with NaOH during the acidification phase. During the basification phase, the pH was allowed to change freely. The bacteria were collected [after] around 16–17 h of culture. The final optical density was approximately 10 units, and the final pH was 8. The culture was then concentrated by filtration using hollow fibers (Amicon), until a final volume of 2 L was obtained. This concentrate of bacteria was then used for the purification of the proteins. After cell concentration, the cells are ground continuously by means of a ball mill, and the ground cell product receives the addition of PMSF 1 mM.

c) Purification of the DNA Polymerase of Pyrococcus sp. GE 5

After centrifugation of the ground cell product (15 min at 10,000 G), the supernatant (soluble fraction) is recovered and heated for 15 min at 75° C. The precipitate which forms after thermal denaturation is eliminated by centrifugation (15 min at 10,000 G). The supernatant is loaded on an anion-exchange column:

Matrix Q Sepharose Fast Flow in an XK 16/30 column (Pharmacia).

Chromatographic system: Bio Pilot (Pharmacia).

Buffer A: Tris HCl 50 mM, pH 8 and buffer B: Tris HCl 50 mM, pH 8+NaCl 0.5M.

Flow rate: 10 mL/min; gradient 0–50% B over 60 min.

Fractions: 10 mL/tube.

Figure 7:
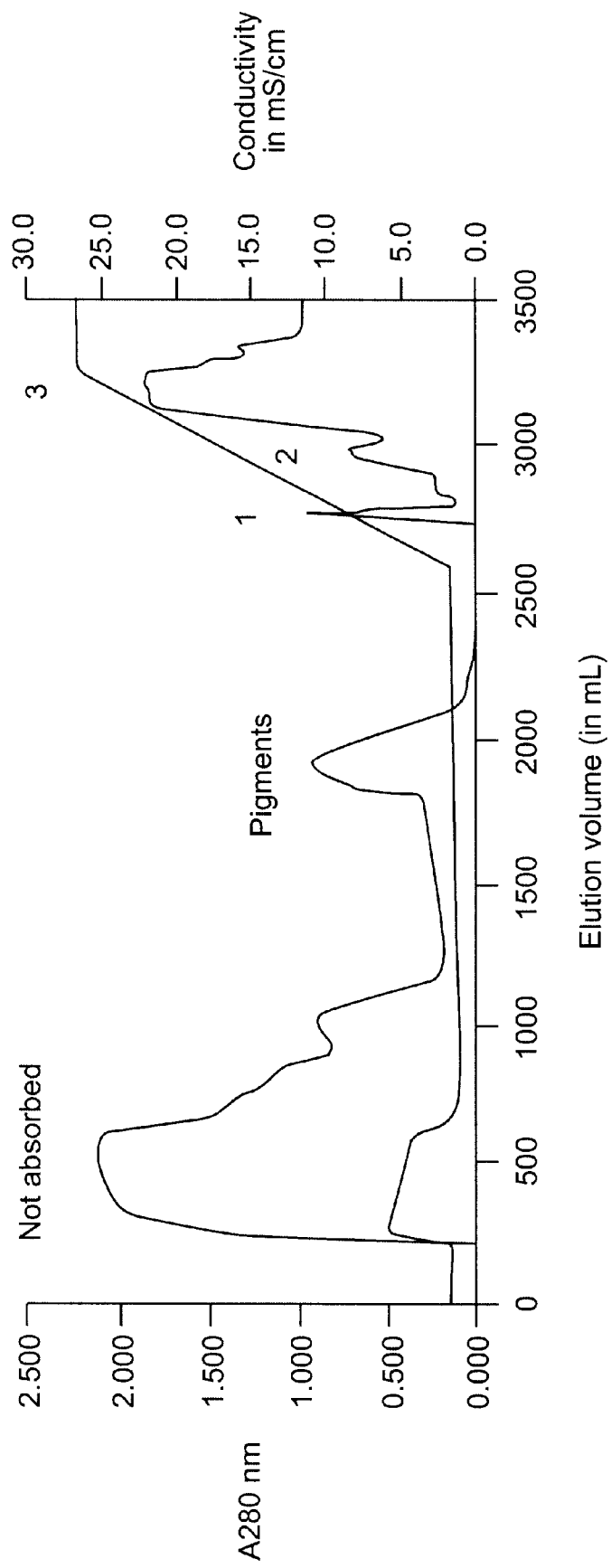
FIG. 7 represents the elution profile of the sample consisting of 450 mL of soluble proteins after thermal denaturation at 75° C. obtained during purification of the DNA polymerase of Pyrococcus sp. GE 5.

FIG. 7 represents the elution profile of the sample consisting of 450 mL of soluble proteins after thermal denaturation at 75° C.

Figure 8:
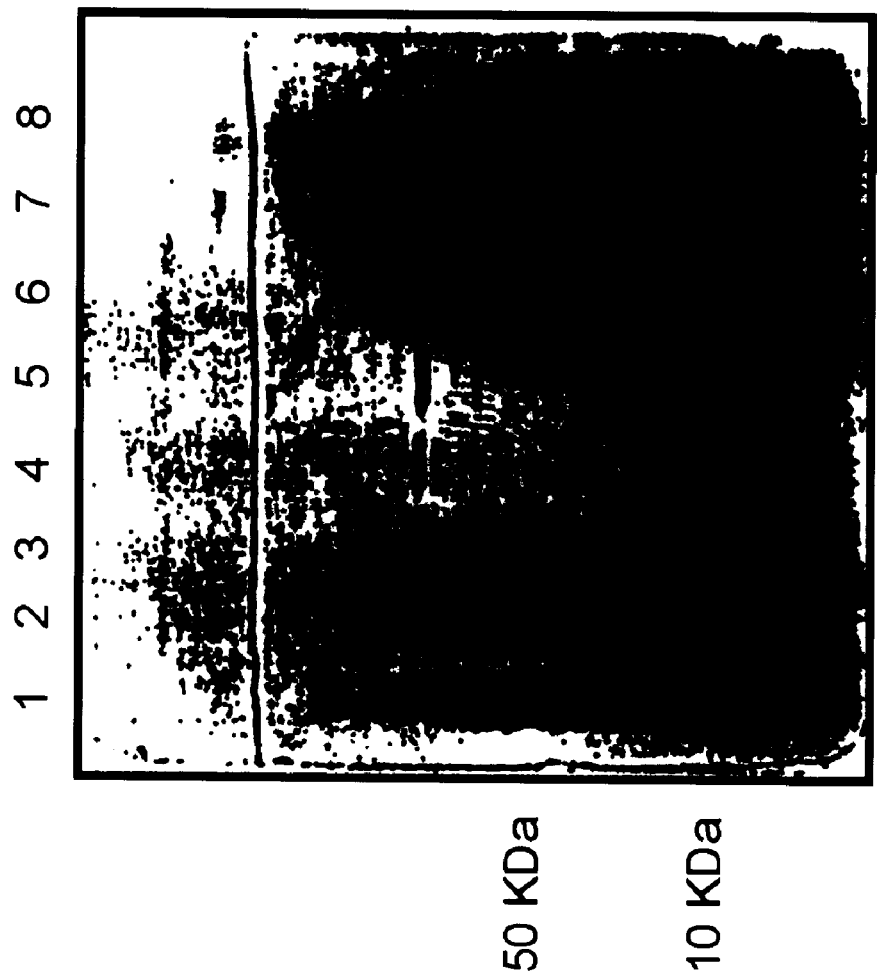
FIG. 8 represents the analysis by SDS-PAGE (Phast System, Pharmacia), in the presence of β-mercaptoethanol, of different fractions coming from the purification of the DNA polymerase of Pyrococcus sp. GE 5.

FIG. 8 represents the analysis by SDS-PAGE (Phast System, Pharmacia), in the presence of β-mercaptoethanol, of different fractions coming from the purification:

Gels: Phast gel 8–15% (Phast System, Pharmacia).

Lanes 1 and 8: molecular weight marker (10 kd, Bio-Rad).

Lane 2: Total proteins.

Lane 3: soluble proteins after grinding.

Lane 4: soluble proteins after thermal denaturation.

Lanes 5, 6, and 7: fractions 1, 2, and 3 after chromatography using QFF of FIG. 2.

As illustrated by FIG. 8, the DNA polymerase of Pyrococcus sp. GE 5 is soluble and thermostable. It is eluted towards 0.15 M NaCl in the ion exchange chromatography. The fractions containing the DNA polymerase of Pyrococcus sp. GE were collected (fraction 2; 50 mL) and subjected to chromatography using hydroxyapatite (type II, Biorad):

Matrix: hydroxyapatite type II in a 10/5 column (Biorad).

Chromatographic system: FPLC (Pharmacia).

Buffer A: Phosphate 50 mM pH 8; buffer B: Phosphate 500 mM pH 8.

Flow rate: 10 mL/min; gradient 0–100% B over 30 min.

Figure 9:
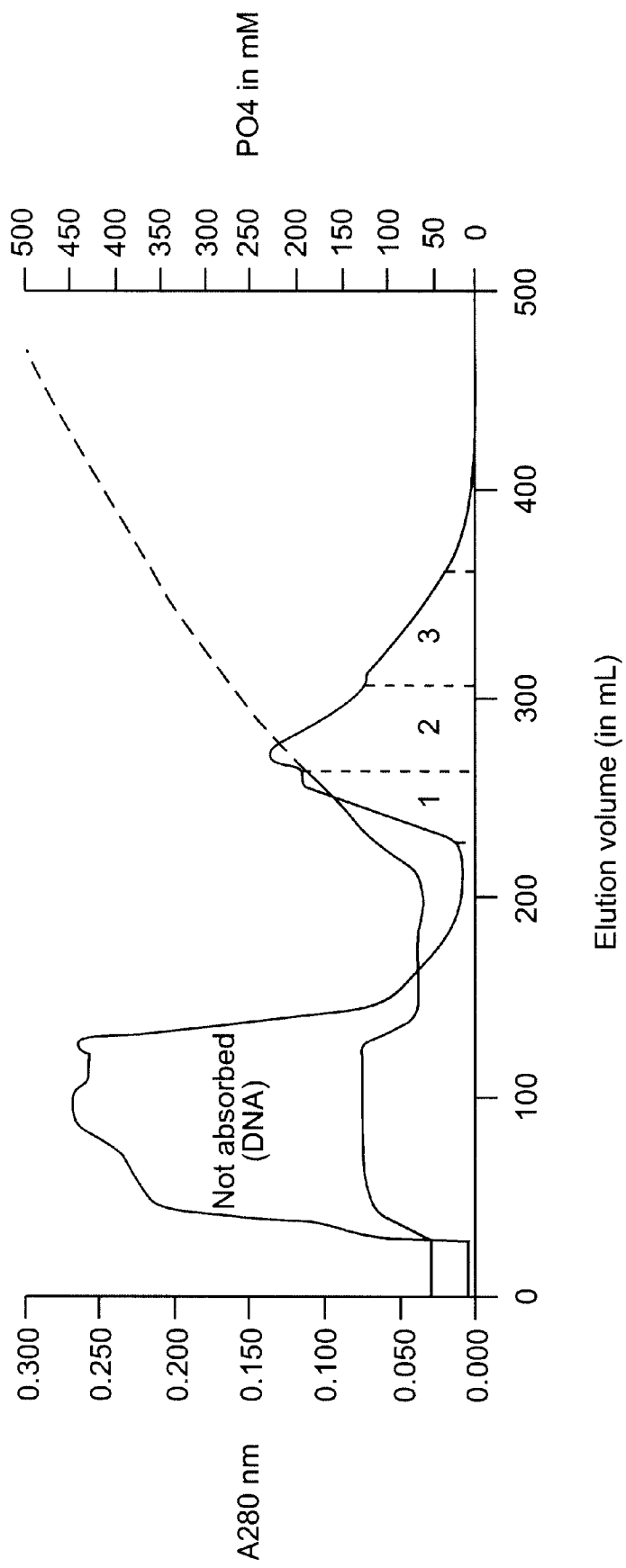
FIG. 9 represents the elution profile for the sample consisting of 50 mL of the fraction containing the DNA polymerase of Pyrococcus sp. GE 5 (fraction 2) after ion-exchange chromatography.

FIG. 9 represents the elution profile for the sample consisting of 50 mL of fraction 2 after ion-exchange chromatography. The different fractions were analyzed by UV spectrometry and by SDS-PAGE. The nonabsorbed fraction mainly contains nucleic acids, whereas the fractions 1 to 3 contain the DNA polymerase of Pyrococcus sp. GE 5. After chromatography, 1 mM of [β-]mercaptoethanol, 0.1% Tween 20 and 50% glycerol were added before storage at −20° C.

d) Characterization of the Purified Fractions

The 3 fractions obtained after chromatography using hydroxyapatite were analyzed by SDS-PAGE in the presence of 2-mercaptoethanol (FIG. 10):

Gels: gel 15% (Laemli, Babygel).

Lanes 1 and 5: Molecular weight marker (Biorad, Broad Range).

Lane 2: Fraction 1 (5 μL).

Lane 3: Fraction 2 (5 μL).

Lane 4: Fraction 3 (5 μL).

Lane 6: Fraction 1 (10 μL).

Lane 7: Fraction 2 (10 μL).

Lane 8: Fraction 3 (10 μL).

Figure 10:
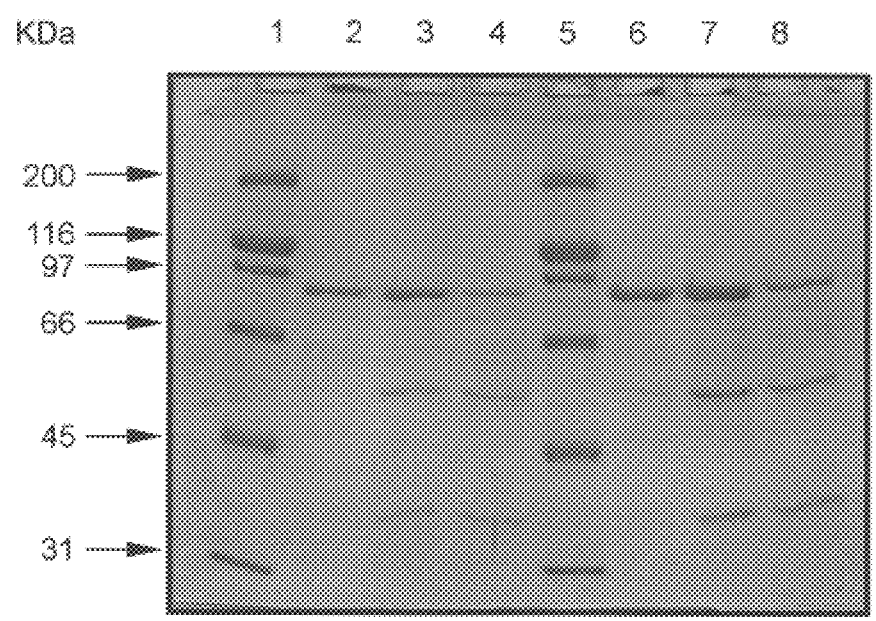
FIG. 10 shows the 3 fractions obtained during purification of the DNA polymerase of Pyrococcus sp. GE 5 after chromatography using hydroxyapatite and analysis by SDS-PAGE in the presence of 2-mercaptoethanol.
Figure 11:
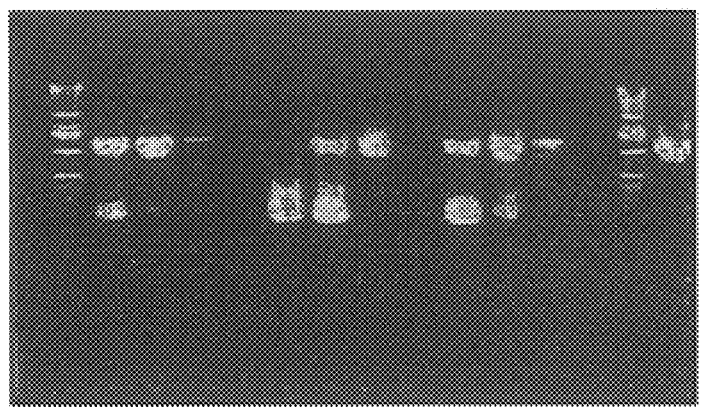
FIG. 11 shows that fraction 1 contains the DNA polymerase of Pyrococcus sp. GE 5 homogenized by SDS-PAGE, while fractions 2 and 3 are contaminated by 2 35-kd and 65-kd proteins.

As illustrated by FIG. 10 and in FIG. 11, fraction 1 contains the DNA polymerase of Pyrococcus sp. GE 5 homogenized by SDS-PAGE, while fractions 2 and 3 are contaminated by 2 35-kd and 65-kd proteins.

e) Activity of the Purified Fractions

The activity of DNA polymerase of the different fractions was tested in a PCR-type amplification reaction. An approximately 1300-bp fragment was amplified using a target DNA and specific primers. The buffer used is composed of:

Tris HCl: 75 mM pH 9.0.

$(NH_4)_2SO_4$: 20 mM.

0.01% (wt/vol) Tween 20.

$MgCl_2$: 1.5 mM.

Thirty-five cycles were done, each including a denaturation step of 1 min at 94° C., a step of pairing of the oligonucleotides of 1 min at the appropriate temperature, and an elongation step of 3 min at 72° C. FIG. 11 reports the results obtained with a reaction volume of 100 μL for quantities of DNA polymerase of Pyrococcus sp. GE 5 of 2.5 μg, 1 g, 0.1 g, and 0.01 μg:

Well No. 1: 1-kb ladder DNA (Gibco BRL).

Well No. 2: fraction 1 (2.5 μg).

Well No. 3: fraction 1 (1 μg).

Well No. 4: fraction 1 (0.1 μg).

Well No. 5: fraction 1 (0.01 μg).

Well No. 6: fraction 2 (2.5 μg).

Well No. 7: fraction 2 (1 μg).

Well No. 8: fraction 2 (0.1 μg).

Well No. 9: fraction 2 (0.1 μg).

Well No. 10: fraction 3 (2.5 μg).

Well No. 11: fraction 3 (1 μg).

Well No. 12: fraction 3 (0.1 μg).

Well No. 13: fraction 3 (0.01 μg).

Well No. 14: 1-kb ladder DNA (Gibco BRL).

Well No. 15: Positive control with *Taq* polymerase.

6) Conditions of Optimization of the PCR for the Polymerases of the Invention

In order to simplify the disclosure of the results hereafter and of the figures relating to them, the thermostable DNA polymerases of *Pyrococcus abyssi* (Pyrococcus sp. GE 5) and Pyrococcus sp. GE 23 will be respectively designated hereafter as Pab and Ppr.

PCR tests were performed under the following conditions:

10 mM Tris HCl, pH 9.0

50 mM KCl 3 mM $MgSO_4$ 0.1% Tween 0.312 mM of each dNTP 50 mol of each oligonucleotide with formula:

5'TCACCTTAGGGTTGCCCATAA3'(SEQ ID NO:9)

5'TGGGCATAAAAGTCAGGGCAG3'(SEQ ID NO:10)

Figure 12:
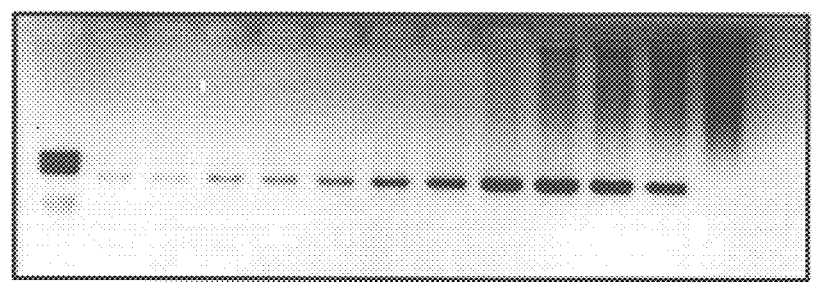
FIG. 12 represents the PCR products loaded on 2% agarose gel in the presence of the pBR marker digested by HaeIII obtained during purification of the DNA polymerase of Pyrococcus sp. GE 5.
Figure 13:
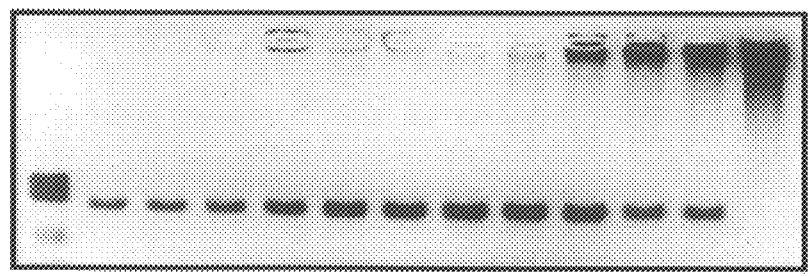
FIG. 13 represents the PCR products loaded on 2% agarose gel in the presence of the pBR marker digested by HaeIII obtained during purification of the DNA polymerase of Pyrococcus sp. GE 5.

1 U of Pab (FIG. 12) or of Ppr (FIG. 13)

Increasing quantity of human genomic DNA of β-globin (from 0.5 ng to 3 μg); reaction volume: 50 μL.

The following PCR program was used:

5 min at 93° C.

37 times (1 min at 62° C.; 2 min at 72° C.; 1 min at 91° C.)

1 min at 62° C.

10 min at 72° C.

FIGS. 12 and 13 represent the PCR products loaded on 2% agarose gel in the presence of the pBR marker digested by HaeIII.

The chosen primers enable one to amplify a 420-bp fragment. Pab and Ppr enable one to obtain a 420-bp PCR product regardless of the quantity of template between 0.5 ng and 1 μg. A PCR product was also obtained under these same conditions in the presence of 10 pg of DNA template.

7) Amplification Capability of Pab and Ppr at High Temperatures

The tests of activity of the recombinant polymerases of *Pyrococcus abyssi* (Pab) and of Pyrococcus sp. GE 23 (Ppr) done using the method of incorporation of labeled dNTP demonstrated, under the buffer conditions used, a residual activity up to 85° C. Beyond this temperature, possible degradation of the substrate could mask the activity of the polymerases of the invention. It is of interest however to evaluate whether this ability can be taken advantage of for in vitro gene amplification, knowing that certain specific applications could proceed from this:

PCR using templates having blocking secondary structures at the usual elongation temperatures of 72 to 74° C., Direct reverse PCR using a double-stranded circular template (chromosome).

Figure 14:
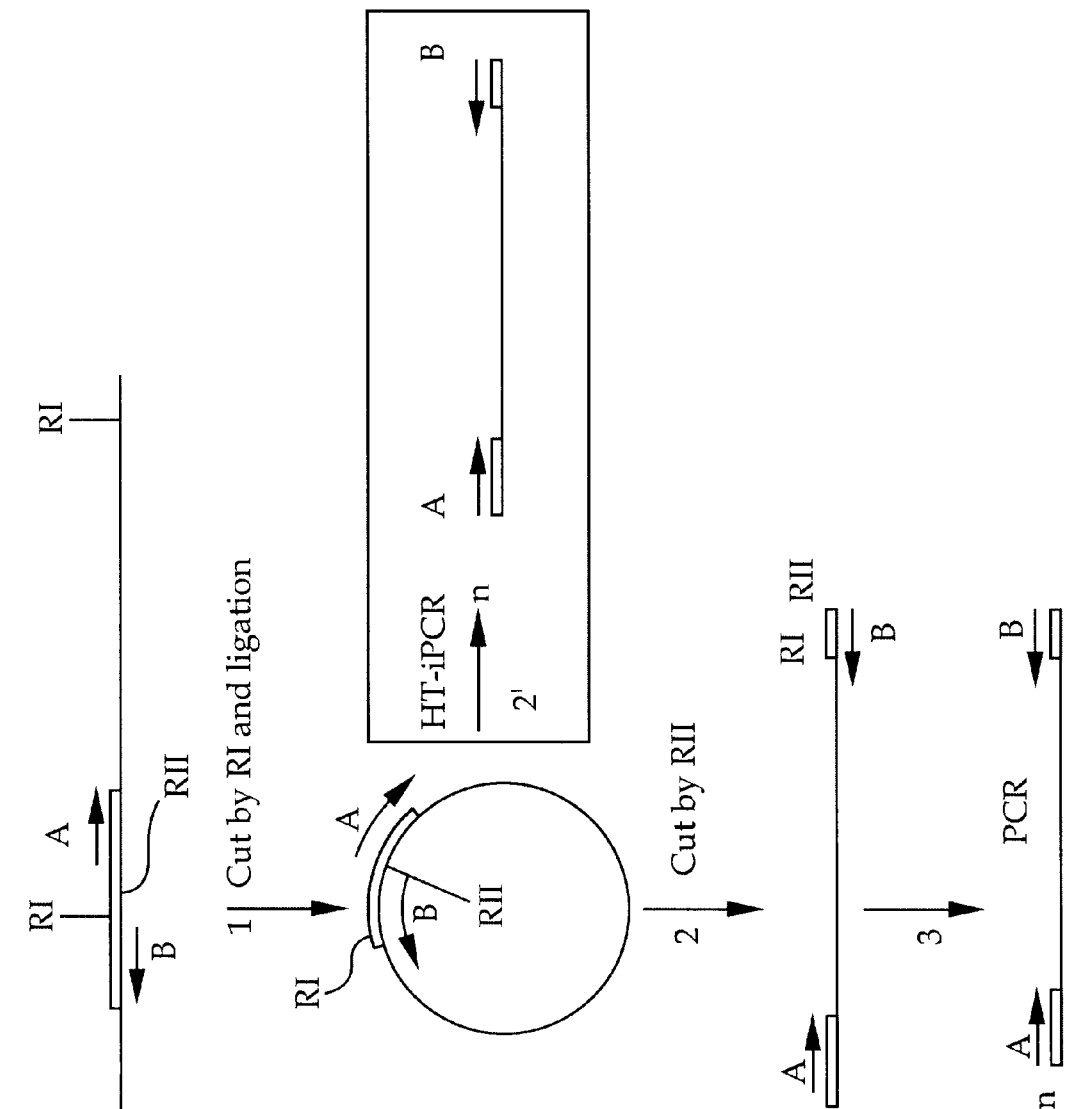
FIG. 14 shows the principles of inverse PCR (iPCR) and of the new method worked out with Pab, called high-temperature inverse PCR (HT-iPCR).

The principles of inverse PCR (iPCR) and of the new method worked out with Pab, called high-temperature inverse PCR (HT-iPCR) are represented in the diagrams of FIG. 14. A double strand of DNA, with a partially known sequence represented "in bold" in FIG. 14, is cut by a restriction enzyme [Eco]RI, diluted and ligated in order to form a double-stranded circular DNA molecule.

In conventional inverse PCR (procedure indicated as 1, 2 and 3 in FIG. 14), the circular molecules are linearized by RII and the amplification is done using the linearized DNA. In HT-iPCR, the amplification is done using the circular molecules (procedure indicated by 2' in FIG. 14).

a) Materials and Methods

The DNA template used for these studies is a 2.2-kb circular DNA fragment. This fragment is obtained by digestion of the genomic DNA of the Thermococcus sp. GE 8 isolate by the enzyme Xho[I], purification using 0.8% agarose gel and elution of the 2 to 2.5-kb band by the GeneClean method, then ligation of the ends of the linear fragments by T4 ligase. The oligonucleotide primers are chosen from the known sequence region of this circularized fragment so as to copy from the known region towards the unknown sequence region (FIG. 14).

The amplification cycles were carried out with a [96-] wellthermocycler of the company Stratagene under the following conditions:

HT-iPCR with a single cycle at 85° C.:
94° C., 15 sec/1 cycle
94° C., 15 sec/56° C., 45 sec/85° C., 4 min/1 cycle
94° C., 15 sec/56° C., 45 sec/82–78° C., 4 min/1 cycle
94° C., 15 sec/56° C., 45 sec/76–72° C., 4 min/1 cycle
94° C., 15 sec/56° C., 45 sec/72° C., 4 min/27 cycles HT-iPCR continuous at 85° C.:
94° C., 15 sec/1 cycle
94° C., 15 sec/56° C., 45 sec/85° C., 4 min/30 cycles
storage at 4° C.

The results are visualized using 0.8% agarose gel.

Figure 15:
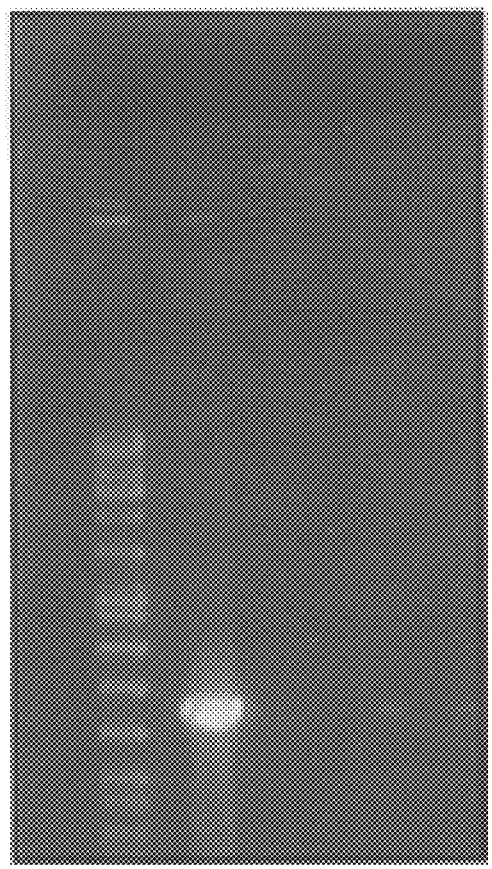
FIG. 15 represents the comparison of the results of iPCR and HT-iPCR using *Taq* and Pab: lane 1: "Raoul" marker; lane 2: HT-iPCR with Pab; lane 3: HT-iPCR with *Taq*; and lane 4: i PCR with *Taq*.

FIG. 15 represents the comparison of the results of iPCR and HT-iPCR using *Taq* and Pab:

lane 1: "Raoul" marker (company Appligene-Oncor)
lane 2: HT-iPCR with Pab
lane 3: HT-iPCR with *Taq*
lane 4: i PCR with *Taq*.

Figure 16:
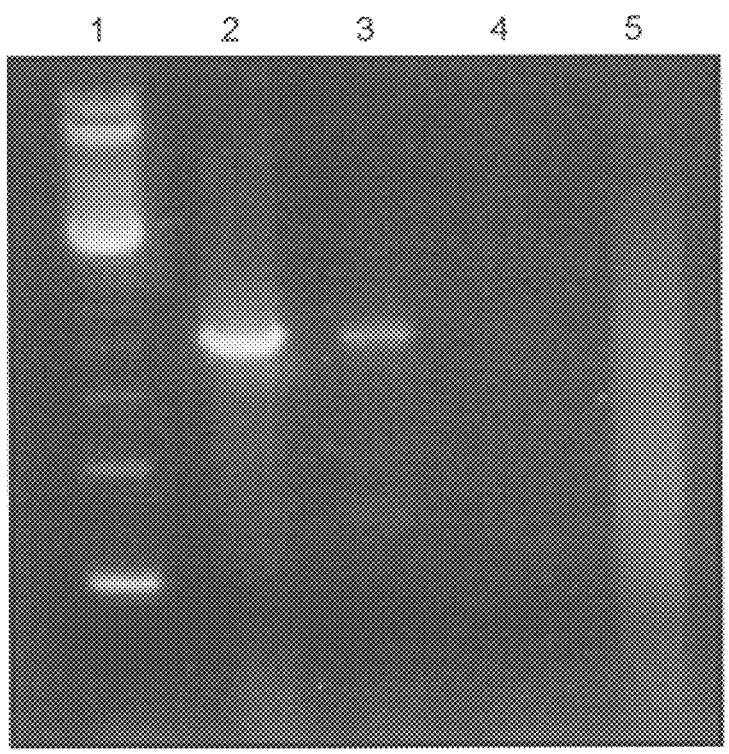
FIG. 16 represents PCR at high temperature (elongation at 85° C. using 30 cycles): lane 1: "Raoul" marker; lane 2: Pab; lane 3: Ppr; lane 4: control without DNA; and lane 5: Vent.
Figure 17:
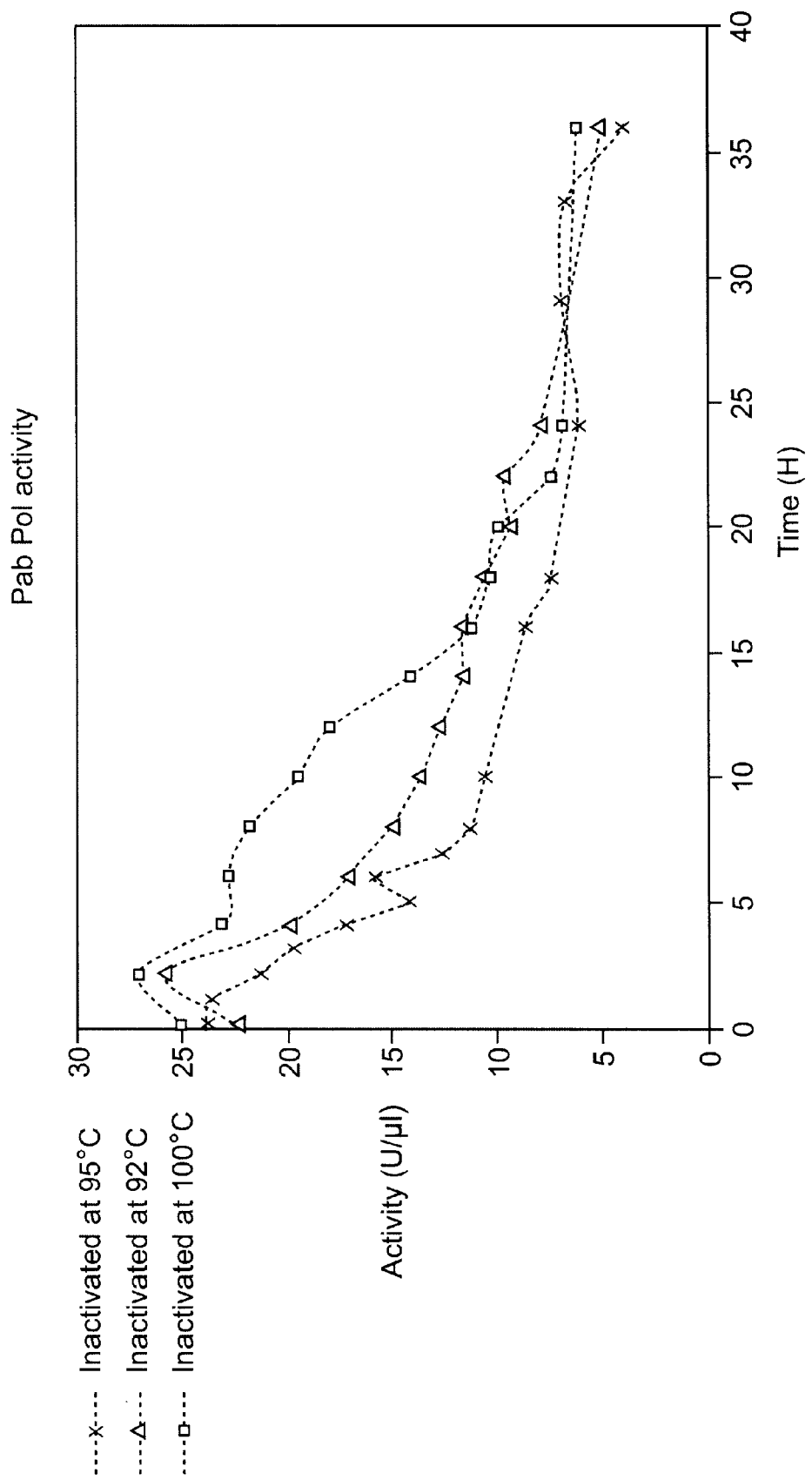
FIG. 17 shows DNA polymerase Pab activity at three temperatures 92° C., 95° C. and 100° C.

FIG. 16 represents PCR at high temperature (elongation at 85° C. using 30 cycles):

lane 1: "Raoul" marker (company Appligene-Oncor)
lane 2: Pab
lane 3: Ppr
lane 4: control without DNA
lane 5: Vent.

b) Results

The results of inverse PCR with a single initial high temperature elongation cycle (85° C.) reveal an excellent behavior of Pab, and an inability of *Taq* (Perkin-Elmer) to perform this type of reaction. The control inverse PCR after linearization of the template by *Taq* provides a signal of low amplitude under the chosen conditions (FIG. 15).

The results obtained with 30 amplification cycles with elongation temperatures of 85° C. reveal an excellent ability of Pab to perform this type of reaction (FIG. 16). Ppr is also capable of amplifying the target DNA under these conditions, but Vent polymerase is incapable as is Pfu.

The results reported above make remarkable applications of the polymerases of the invention possible.

On one hand, the amplification is possible of DNA fragments which have secondary structures making elongation at temperatures of 72–74° C. difficult. The temperature rise up to 85° C. allows one to resolve these secondary structures which can form on single strands in the step of hybridization of the primers.

On the other hand, it is possible to use this on a chromosome when a small part of a sequence of a gene is known. The method disclosed above is generally applied as follows:

digestion of the genomic DNA by several restriction enzymes,
ligation by a ligase, such as T4 ligase, of the digestion products, HT-iPCR using primers in the opposite direction on the known sequence region using Pab or Ppr,
possibly sequencing of the amplification products.

8) Study of the Thermostability of the Recombinant Enzymes of the Invention a) Materials and Methods In order to perform the tests necessary for this study, the DNA polymerases Pab and Ppr are diluted in a conditioning buffer (20 mM Tris HCl pH=8.0; 0.1 mM EDTA; 1 mM dithiothreitol; 50% glycerol; 0.5% Tween 20; 0.5% Nonidet 40; 0.2 mg/mL BSA), in such a way as to add 0.01 U of polymerase per test and to put oneself under nonsaturating conditions. Thus, 0.01 U of Pab or of Ppr are incubated in 20 $\mu$L of incubation buffer (10 mM Tris HCl pP=9.0; 50 mM KCl; 3 mM MgSO$_4$; 0.1% Tween) for different times (0 to 36 h), at 92° C., at 95° C. or at 100° C. The same number of test tubes as the number of different incubation times was prepared from the same initial mixture. The different tubes are incubated in a dry bath (PCR unit). At the end of incubation, the tubes are put in ice and the residual activity of the enzyme will be measured at 72° C. as described hereafter.

The activity test is performed in a final volume of 100 $\mu$L of incubation buffer (10 mM Tris HCl pP=9.0; 50 mM KCl; 3 mM MgSO$_4$; 0.1% Tween) under the following conditions:

13 $\mu$g of activated calf thymus DNA
500 $\mu$M of each of 4 dNTP
10 $\mu$Ci of one of the four DNTP labeled with $^{32}$P used as marker (dATP or dNTP were used)
20 $\mu$L of the solution corresponding to the test of inactivation by temperature.

The tests are incubated for 30 min at 70° C. 10 FL of each test are removed after 10 min, 20 min, and 30 min of incubation, and are then deposited on DE81 paper (Whatmann). Condensing before washing is then done dry by the Cerenkov method. The DE81 papers are then washed three times for 5 min in 0.5 mM solution of Na$_2$HPO$_4$ in order to eliminate the unincorporated DNTP. A passage with alcohol makes possible rapid drying of the papers which are counted again. A negative control (To) is done without DNA polymerase, and a positive control is done with DNA polymerase not temperature treated, corresponding to time 0 h. A polymerase unit is the quantity of enzyme necessary for the incorporation of 10 nmol of nucleosides in acid-soluble products in 30 min at 72° C. under the test conditions. The polymerase activity is calculated by taking the average of the total counts before washing in 10 $\mu$L of deposit. They correspond to 4×5 nmol of each dNTP, or 20 nmol of dNTP total. From each value after washing (Ci), it is necessary to subtract the value of the negative control To (without enzyme).

Let, U/EL=(Ci—To)×(30 min/incubation time)×((100 $\mu$L/10 $\mu$L deposit)×(polymerase dilution)Ct for 10 nmol)×$\mu$L of polymerase added b) Results.

The two enzymes were studied at three temperatures 92° C., 95° C. and 100° C. All the studies were done in parallel with the same substrates. The results are represented in the curves of FIGS. 17 to 20. For FIGS. 19 (Table V hereafter) and 20 (Table VI hereafter), the different polymerases studied are reduced to the same basis with regard to the initial activity, in order to facilitate the comparative study. A fourth temperature of 105° C. was also studied for Pab but is not illustrated in the figures.

Figure 19:
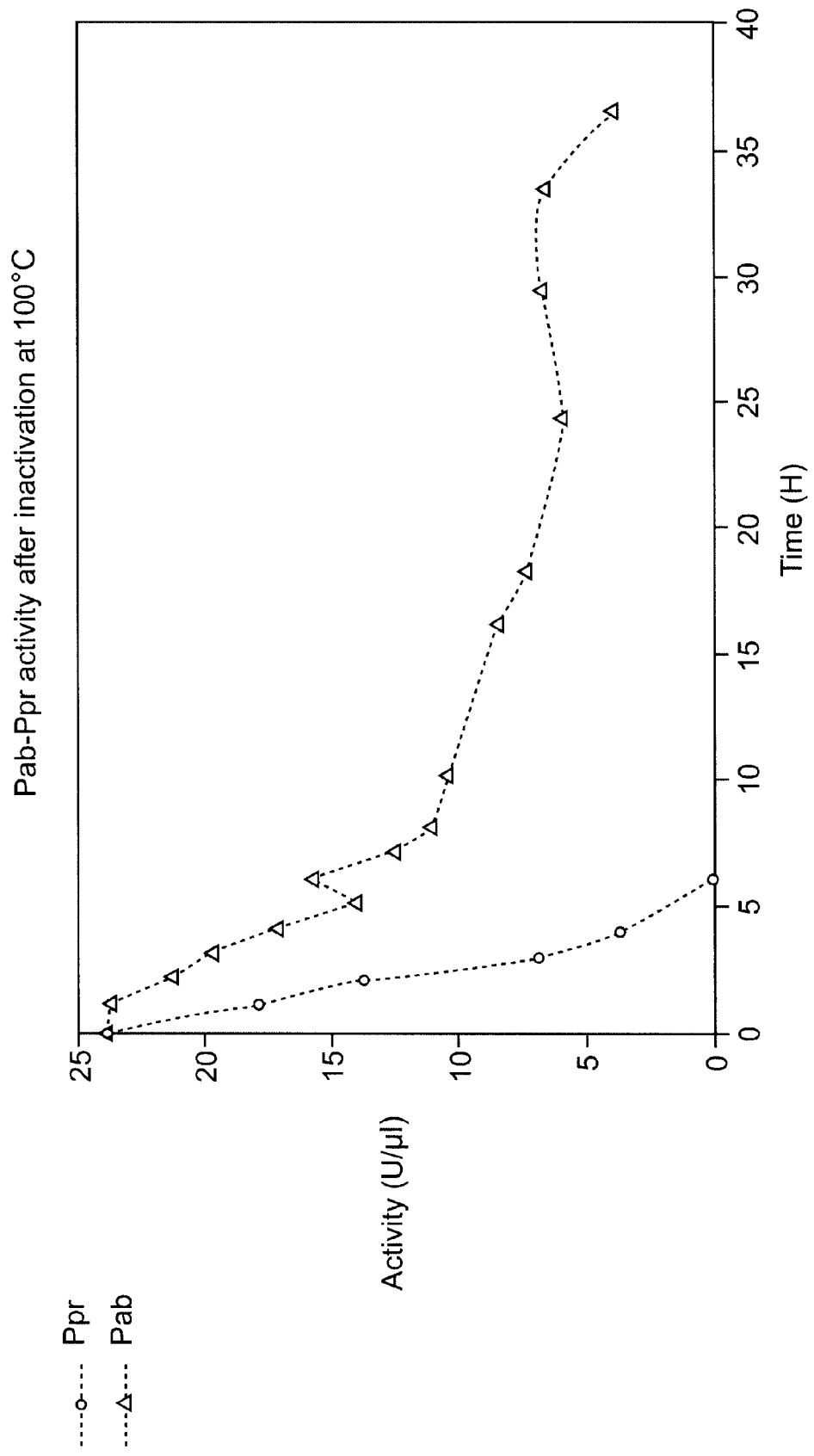
FIG. 19 shows DNA polymerase Pab and Ppr activity after inactivation at 100° C.

FIG. 19: Pab activity

Table III below reports the results of the inactivation of the Pab as a function of time at 100° C., 95° C. and 92° C.

TABLE III

| Temps (hours) | Inactivation at 100° C. | Inactivation at 95° C. | Inactivation at 92° C. |
|---|---|---|---|
| 0 | 23,8 | 22.3 | 25 |
| 1 | 23,6 | | |
| 2 | 21,3 | 25,8 | 27,1 |
| 3 | 19,7 | | |
| 4 | 17,2 | 19,9 | 23,1 |
| 5 | 14,1 | | |
| 6 | 15,9 | 17,1 | 22,8 |
| 7 | 12,6 | | |
| 8 | 11,2 | 14,9 | 21,8 |
| 9 | | | |
| 10 | 10,5 | 13,6 | 19,5 |
| 12 | | 12,7 | 18 |
| 14 | | 11,6 | 14,05 |
| 16 | 8,6 | 11,6 | 11,2 |
| 18 | 7,5 | 10,6 | 10,3 |
| 20 | | 9,4 | 9,9 |
| 22 | | 9,7 | 7,5 |
| 24 | 6,2 | 8 | 7 |
| 29 | 7,1 | | |
| 33 | 7 | | |
| 36 | 4,3 | 5,3 | 6,5 |

Figure 18:
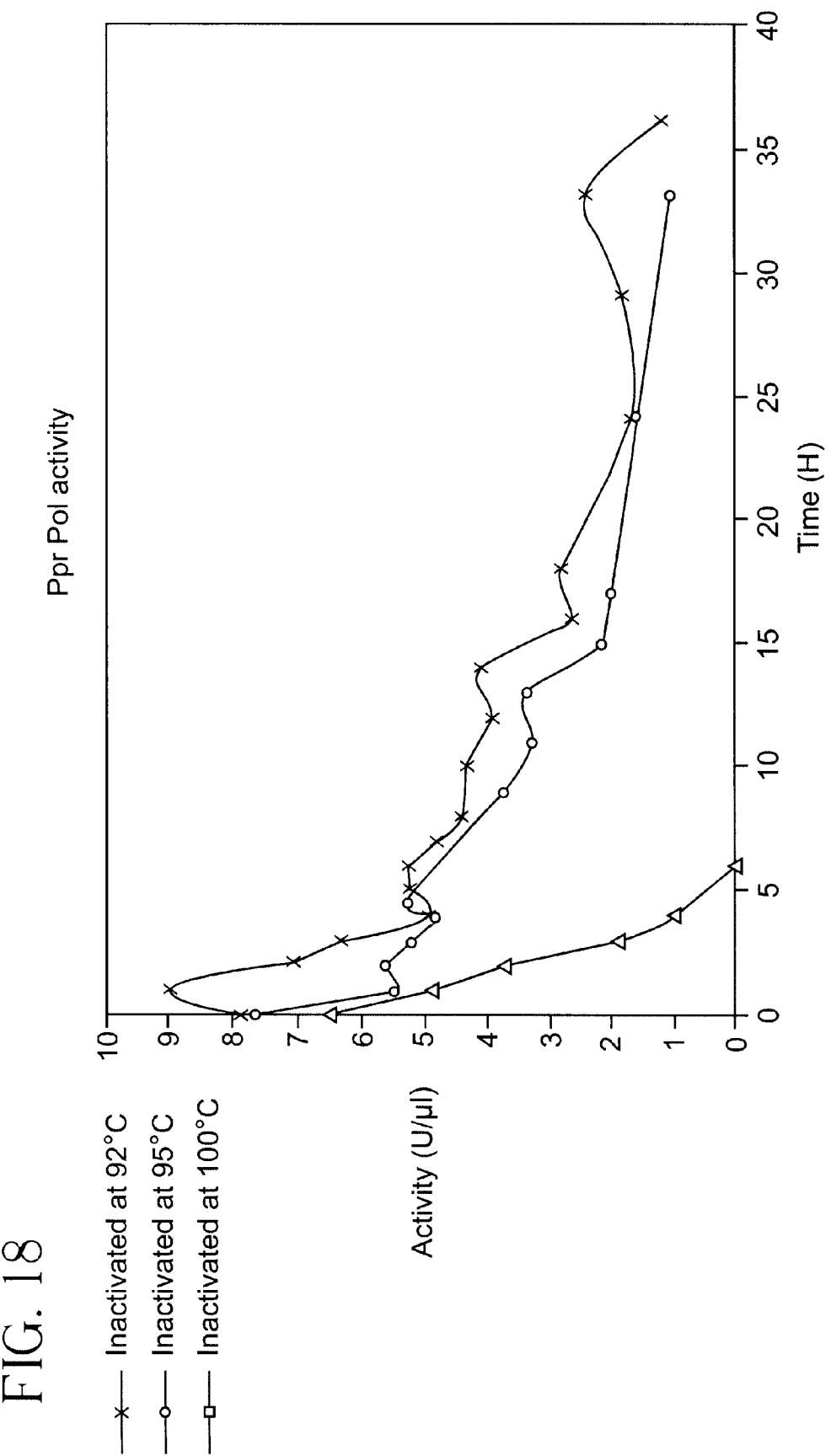
FIG. 18 shows DNA polymerase Ppr activity at three temperatures 92° C., 95° C. and 100° C.

Key: 1 Time (h)
2 Inactivation at 100° C.
3 Inactivation at 95° C.
4 Inactivation at 92° C.
FIG. 18: Ppr activity Table IV below reports the results of the inactivation of the Ppr as a function of time at 100° C., 95° C. and 92° C.

TABLE IV

| Temps (hours) | Inactivation at 100° C. | Inactivation at 95° C. | Inactivation at 92° C. |
|---|---|---|---|
| 0 | 6,5 | 7,66 | 7,88 |
| 1 | 4,9 | 5,5 | 8,98 |
| 2 | 3,75 | 5,63 | 7,09 |
| 3 | 1,9 | 5,23 | 6,36 |
| 4 | 1 | 4,8 | 4,94 |
| 4,5 | | 5,3 | |
| 5 | | | 5,25 |
| 6 | 0 | | 5,27 |
| 7 | | | 4,8 |
| 8 | | | 4,44 |
| 9 | | 3,75 | |
| 10 | | | 4,34 |
| 11 | | 3,28 | |
| 12 | | | 3,92 |
| 13 | | 3,35 | |
| 14 | | | 4,11 |
| 15 | | 2,14 | |
| 16 | | | 2,63 |
| 17 | | 1,94 | |
| 18 | | | 2,8 |
| 24 | | | 1,65 |
| 29 | | | 1,84 |
| 33 | | 1,06 | 2,46 |
| 36 | | | 1,23 |

Key: 1 Time (h)
2 Inactivation at 100° C.
3 Inactivation at 95° C.
4 Inactivation at 92° C.
FIG. 19: Pab and Ppr activity after inactivation at 100° C.

FIG. 19: Pab and Ppr activity after inactivation at 100° C.

Table V below reports the activity of Pab and Ppr after inactivation at 100° C.

TABLE V

| Temps (hour) | Pab | Ppr |
|---|---|---|
| 0 | 23,8 | 23,8 |
| 1 | 23,6 | 17,9 |
| 2 | 21,3 | 13,7 |
| 3 | 19,7 | 6,9 |
| 4 | 17,2 | 3,7 |
| 5 | 14,1 | |
| 6 | 15,9 | 0 |
| 7 | 12,6 | |
| 8 | 11,2 | |
| 10 | 10,5 | |
| 16 | 8,6 | |
| 18 | 7,5 | |
| 24 | 6,2 | |
| 29 | 7,1 | |
| 33 | 7 | |
| 36 | 4,3 | |

Figure 20:
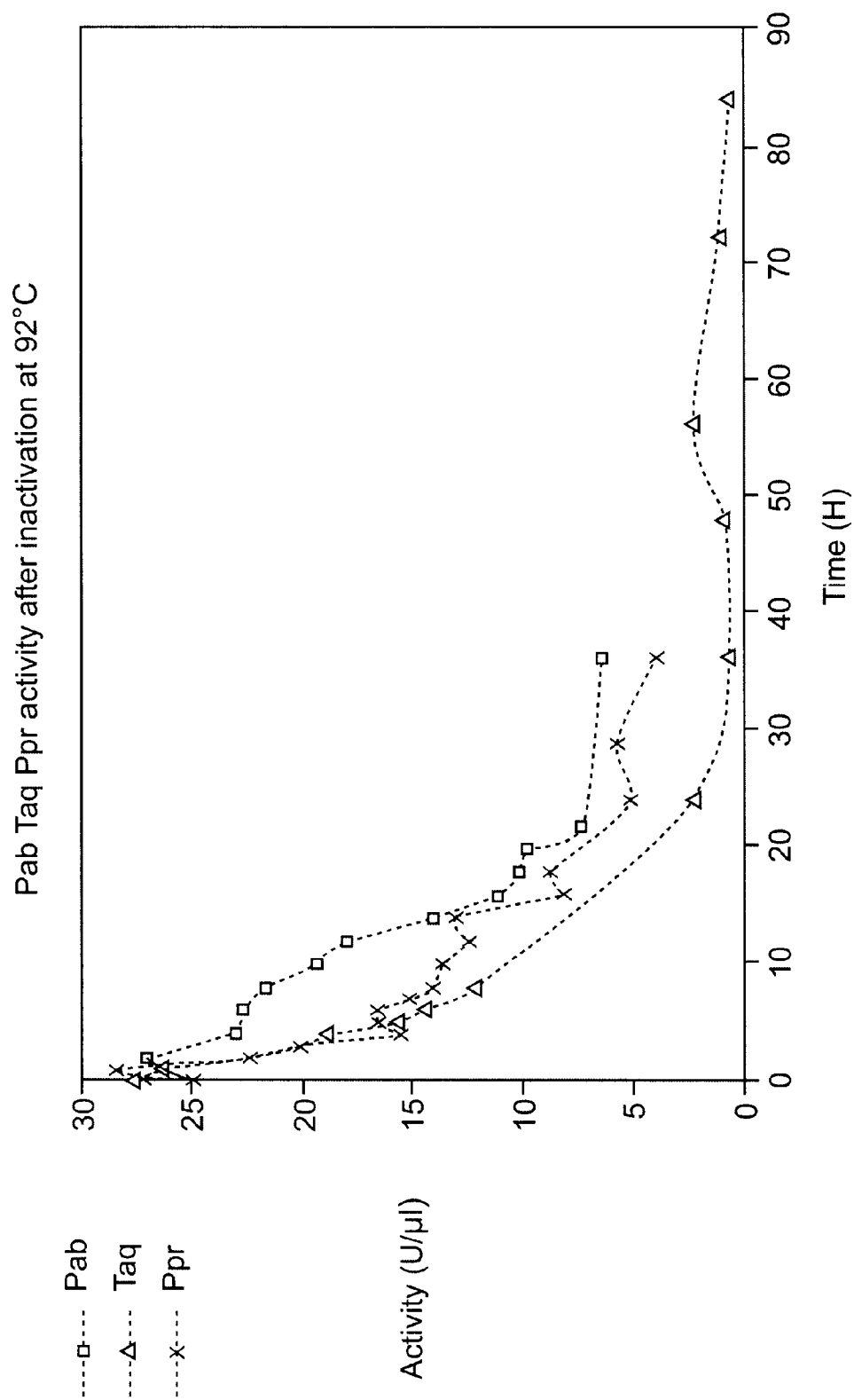
FIG. 20 shows Pab, Ppr and *Thermus aquaticus* (*Taq*) polymerase activity after inactivation at 92° C.

Key: 1 Time (h)
FIG. 20: Pab, Ppr, and *Thermus aquaticus* (Taq) polymerase activity after inactivation at 92° C.

Table VI below reports the activity of Pab, Ppr, and *Taq* after inactivation at 92° C.

TABLE VI

| Temps (hour) | Pab | Taq | Ppr |
|---|---|---|---|
| 0 | 25 | 27,7 | 25 |
| 1 | | 26,5 | 28,5 |
| 2 | 27,1 | 22,5 | 22,5 |
| 3 | | 20,2 | 20,2 |
| 4 | 23,1 | 19 | 15,6 |
| 5 | | 15,7 | 16,6 |
| 6 | 22,8 | 14,5 | 16,7 |
| 7 | | | 15,2 |
| 8 | 21,8 | 12,3 | 14,1 |
| 10 | 19,5 | | 13,7 |
| 12 | 18 | | 12,5 |
| 14 | 14,05 | | 13 |
| 16 | 11,2 | | 8,3 |
| 18 | 10,3 | | 8,9 |
| 20 | 9,9 | | |
| 22 | 7,5 | | |
| 24 | | 2,3 | 5,2 |
| 29 | | | 5,8 |
| 36 | 6,5 | 0,5 | 3,9 |
| 48 | | 0,8 | |
| 56 | | 2,2 | |
| 72 | | 1 | |
| 84 | | 0,7 | |

Key: 1 Time (h)

The analysis of the curves of FIGS. 17 to 20 shows that:
Pab keeps 90% of its activity after a treatment of 5 hs at 92° C, 70% after 5 h at 95° C. and 60% after 5 h at 100° C. Pab keeps 50% of its activity after a treatment of 90 min at 105° C.

Ppr keeps 68% of its activity after 5 h at 92° C., 65% after 5 h at 95° C. and 10% after 5 h at 100° C.

In comparison, *Taq* polymerase keeps 55% of its activity after 5 h at 92° C., but it only has a half-life of 90 min at 95° C. and of 5 min at 100° C.

According to the curves of FIGS. 17 to 20 and the comments above, the enzyme Pab is more thermostable than Ppr in spite of a difference of only ten residues between their sequences. The enzyme Pab is the most thermostable currently described with a half-life at 95° C. of 18 h and more than 8 h at 100° C. The enzyme Ppr has a thermostability comparable with that published for Vent or even better with 2 h half-life at 100° C.

What is claimed is:

1. A DNA polymerase purified from the strain of archaeobacteria of the genus Pyrococcus sp. GE 5 encoded by the nucleotide sequence shown in SEQ ID NO: 3.

2. A DNA polymerase purified from the strain of archaeobacteria of the genus Pyrococcus sp. GE 23 encoded by the nucleotide sequence shown in SEQ ID NO: 1.

3. A thermostable purified DNA polymerase whose amino acid sequence is shown in SEQ ID NO:2.

4. A thermostable purified DNA polymerase whose amino acid sequence is shown in SEQ ID NO:4.

* * * * *